(12) United States Patent
Federation et al.

(10) Patent No.: US 12,276,667 B2
(45) Date of Patent: Apr. 15, 2025

(54) ISOLATION AND CHARACTERIZATION OF THE NUCLEAR PROTEOME

(71) Applicant: Altius Institute for Biomedical Sciences, Seattle, WA (US)

(72) Inventors: Alexander Federation, Seattle, WA (US); John Stamatoyannopoulos, Seattle, WA (US)

(73) Assignee: Altius Institute for Biomedical Sciences, Seattle, WA (US)

( * ) Notice: Subject to any disclaimer, the term of this patent is extended or adjusted under 35 U.S.C. 154(b) by 581 days.

(21) Appl. No.: 16/417,658

(22) Filed: May 21, 2019

(65) Prior Publication Data

US 2020/0033358 A1   Jan. 30, 2020

Related U.S. Application Data

(60) Provisional application No. 62/646,298, filed on Mar. 21, 2018.

(51) Int. Cl.
  *G01N 33/68*  (2006.01)
  *C12N 9/16*  (2006.01)
(52) U.S. Cl.
  CPC ........... *G01N 33/6848* (2013.01); *C12N 9/16* (2013.01); *C12Y 301/31001* (2013.01)

(58) Field of Classification Search
  None
  See application file for complete search history.

(56) References Cited

U.S. PATENT DOCUMENTS

2017/0287687 A1   10/2017   Chang

OTHER PUBLICATIONS

Schnitzler, Curr. Protocols Mol. Biol. Suppl. 50: 21.5.1-21.5.12 (2000).*
Shechter et al., Nature Protocols 2(6): 1445-1457 (2007).*
Rocha et al., J. Biol. Chem. 259(13): 8558-8563 (1984).*
Su et al., Expert Rev. Proteomics 4(2): 211-225 (2007).*
Mieczkowski et al., Nature Communications 7: 11485 (2016).*
Lange et al., Mol. Carcinog. 48(7): 571-580 (2009).*
Federation et al., (2020) "Highly Parallel Quantification and Compartment Localization of Transcription Factors and Nuclear Proteins", Cell Reports, 30:2463-2471.
Teves and Henikoff, Randall H. Morse (ed.), Chromatin Remodeling: Methods and Protocols, Methods in Molecular Biology, vol. 833:421-432, DOI 10.1007/978-1-61779-477-3_25, © Springer Science+Business Media, LLC, 2012.

* cited by examiner

*Primary Examiner* — Erin M. Bowers
(74) *Attorney, Agent, or Firm* — Bozicevic, Field & Francis LLP; Shweta Chandra

(57) ABSTRACT

Disclosed herein are methods for solubilizing and isolating nuclear proteins from cells.

15 Claims, 23 Drawing Sheets

210 — Collect the pelleted chromatin generation by method 100.

220 — Add a cleavable surfactant to the chromatin pellet to form a first solution.

230 — Heat the first solution.

240 — Add a reducing agent to the first solution to obtain a second solution.

250 — Add an alkylating agent to the second solution to obtain a third solution.

260 — Add a trypsin-acetic acid mixture to the third solution to obtain a fourth solution.

270 — Add a strong acid to the fourth solution to obtain a fifth solution.

280 — Clean up the fifth solution.

FIG. 10
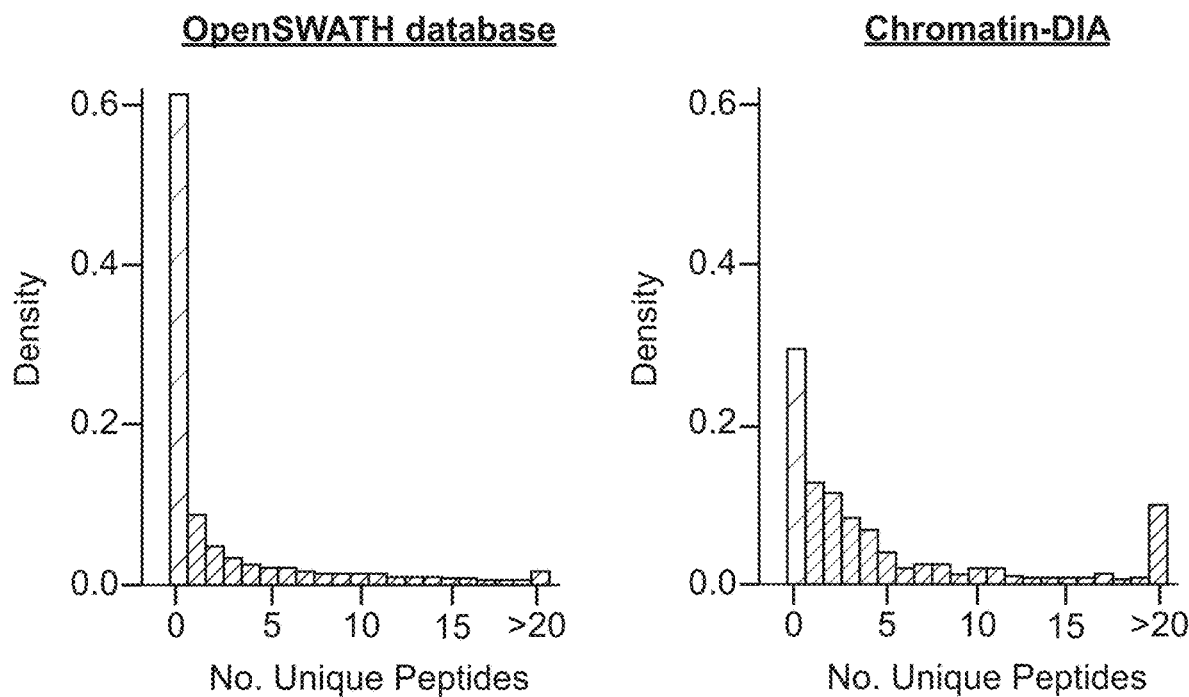
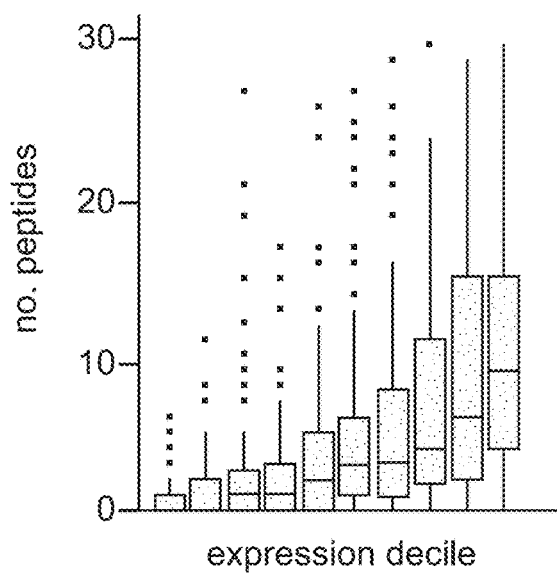

FIG. 11
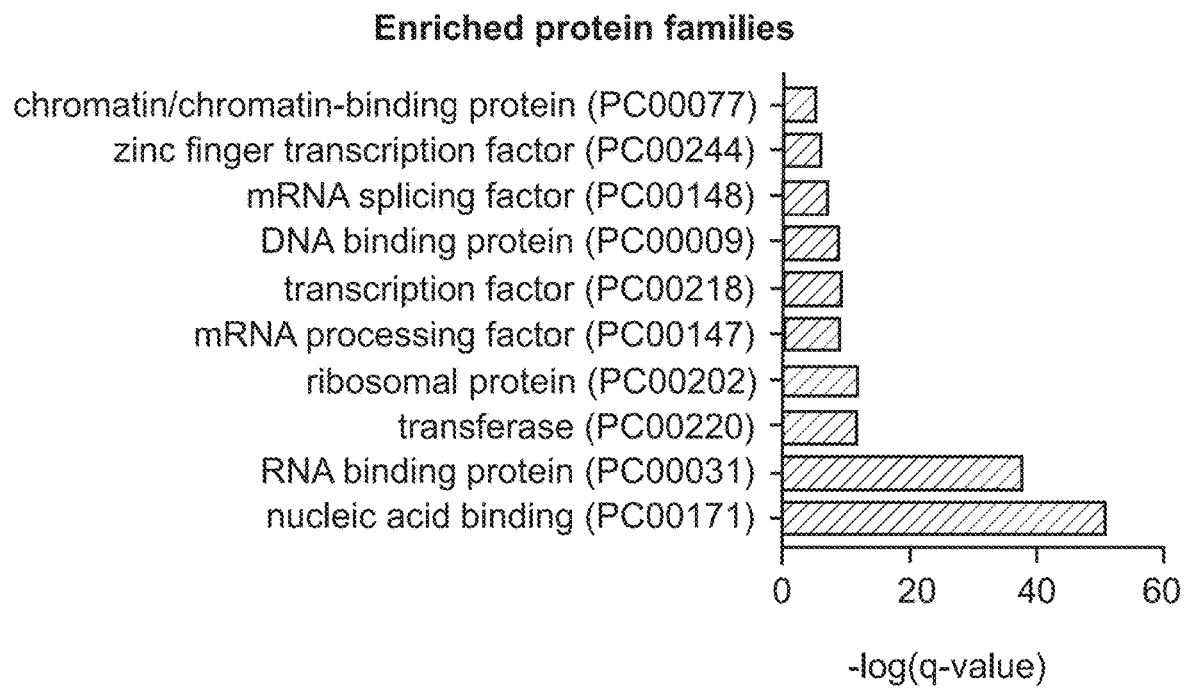
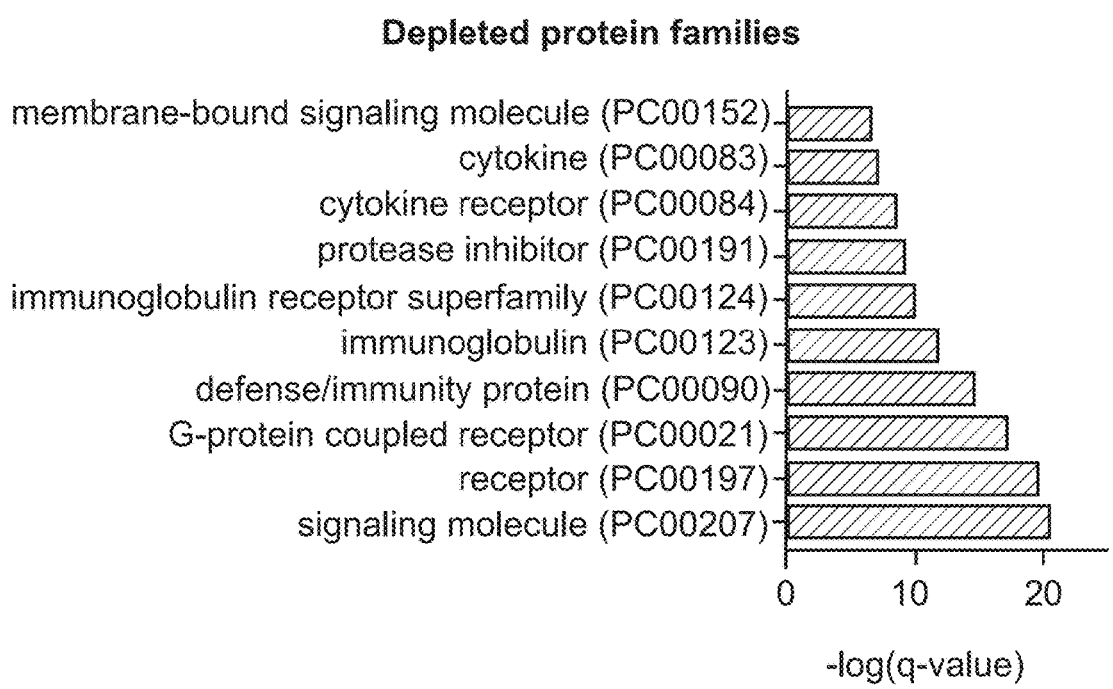

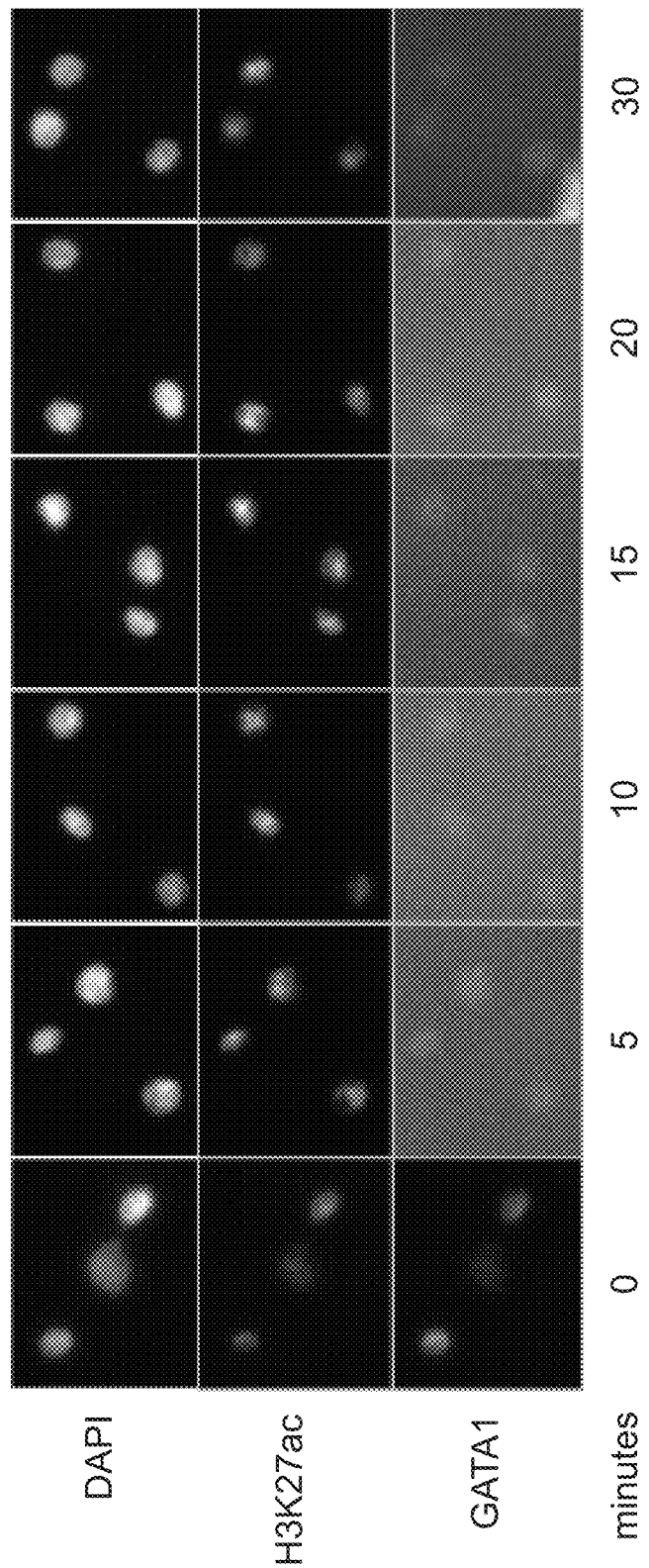

FIG. 12A (Cont.)
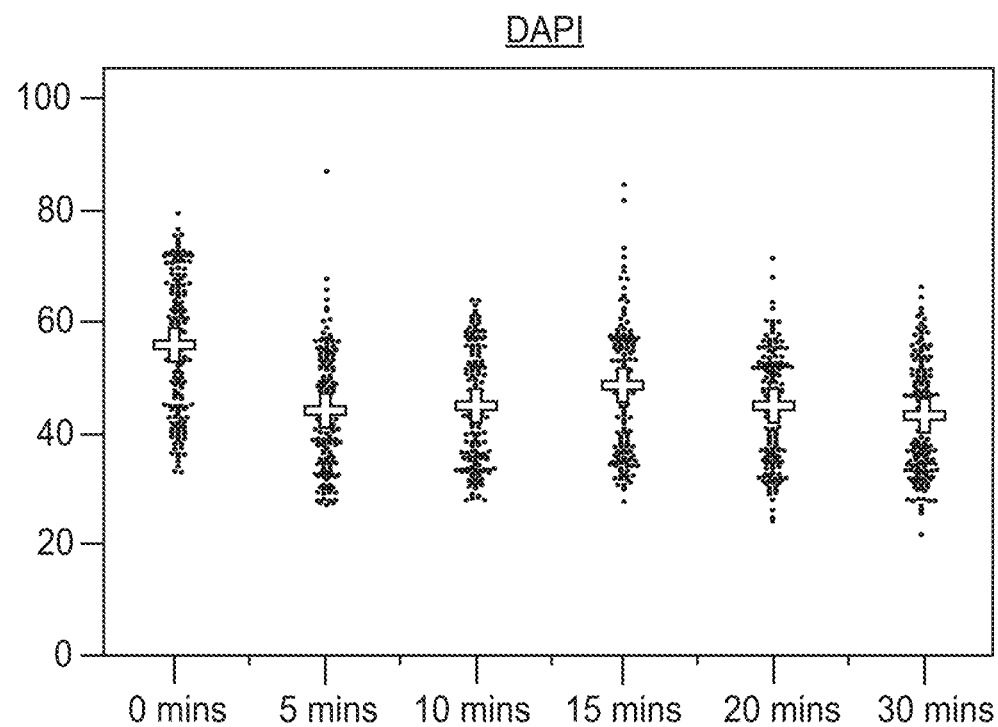
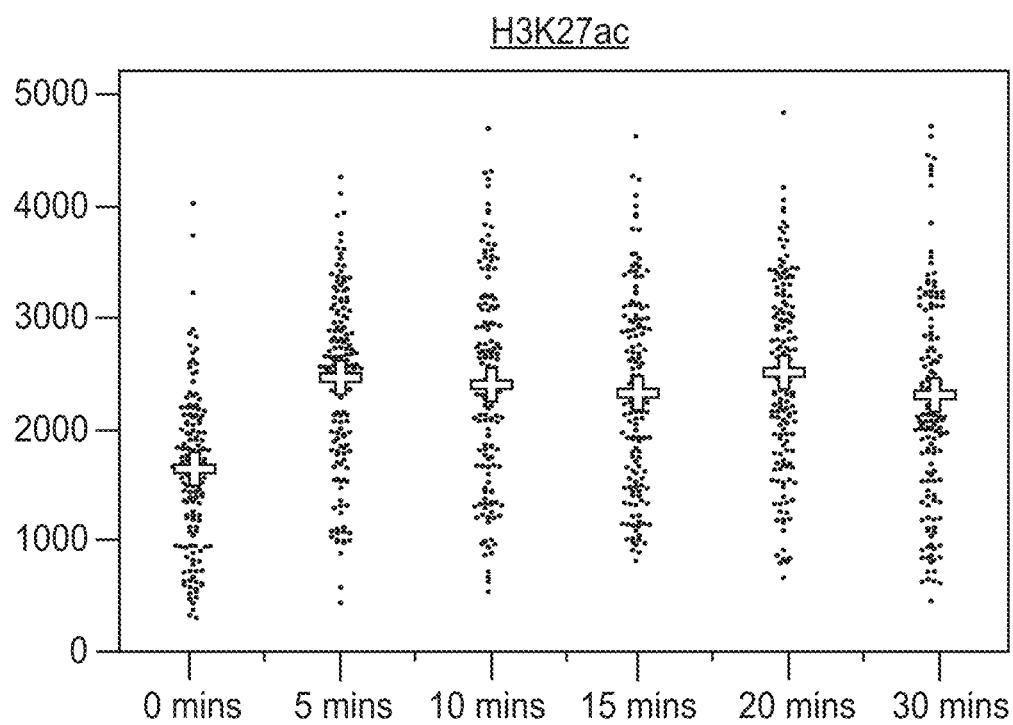

ISOLATION AND CHARACTERIZATION OF THE NUCLEAR PROTEOME

BACKGROUND OF THE INVENTION

Proteins that reside in the nucleus and interact with chromatin have proven especially difficult to characterize with proteomics using prior methods. This is likely because of any of three factors. Firstly, these proteins are often of lower relative abundance compared to structural proteins and histones. Secondly, these proteins are often sequestered by insoluble chromatin. Finally, these proteins often display extensive post-translational modification. Thus, there is a need for systems and methods to alleviate these issues in order to allow proteomic characterization of nuclear proteins.

SUMMARY OF THE INVENTION

Described herein are systems and methods for solubilizing and isolating nuclear proteins from cells. After isolation, these proteins are then subjected to proteomic characterization with data-independent acquisition (DIA), allowing increased sensitivity for low abundance proteins and accurate label-free quantification across samples.

In some aspects, a method for preparing cells to enhance mass spectrometry signals obtained from nuclear proteins comprises: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution.

In some aspects, a method for comparing nuclear proteomes across different conditions comprises: preparing a first sample from a first condition by: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution; and preparing a second sample from a second condition by: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution; and comparing a nuclear proteome determined by mass spectrometry of the first sample prepared by a)-e) to a nuclear proteome determined by mass spectrometry of the second sample prepared by a)-e).

In some aspects, a method for characterizing a small molecule degradation compound comprises providing cells treated with a small degradation compound and then: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution; and characterizing a nuclear proteome determined by mass spectrometry of the treated cells prepared by a)-e).

In some aspects, a method for assaying cellular thermal shifts comprises: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution.

In some aspects, a method for characterizing genome edits comprises providing edited cells and: a) preparing a first suspension solution with buffer A not comprising polycations and a second suspension solution comprising the first suspension solution and a salt; b) adding a detergent solution to isolate the cell nuclei of the cells; c) re-suspending the cells in the second suspension solution; d) quenching the cells; and e) pelleting insoluble chromatin from the second suspension solution; and characterizing a nuclear proteome determined by mass spectrometry of the edited cells prepared by a)-e).

In some embodiments, the method further comprises harvesting, homogenizing, washing, or pelleting the cells between a) and b). In some embodiments, the method further comprises re-suspending the cells in the first suspension solution between a) and b). In some embodiments, the method further comprises spinning or pelleting the cells between b) and c). In some embodiments, the method further comprises incubating the cells between d) and e). In some embodiments, the cells of interest are incubated at a temperature of about 4° C. In some embodiments, the cells of interest are incubated for a period of about 30 minutes. In some embodiments, the method further comprises collecting supernatant liquid from the second suspension solution after e). In some embodiments, a) comprises removing spermidine. In some embodiments, a) comprises removing spermine. In some embodiments, the detergent solution comprises NP40 detergent solution. In some embodiments, the detergent solution is present at a concentration of from 0% to 4% or from 0.01% to 0.1%. In some embodiments, the salt of the second suspension solution comprises sodium chloride (NaCl). In some embodiments, the NaCl is present at a concentration of about 250 nM. In some embodiments, d) comprises quenching the cells with ethylenediaminetetraacetic acid (EDTA). In some embodiments, the EDTA is present at a concentration of from 0.1 mM to 10 mM. In some embodiments, the method further comprises treating the cells micrococcal nuclease (MNase). In some embodiments, the cells of interest are treated with MNase at a temperature of about 37° C. In some embodiments, the cells of interest are treated with MNase for a period of about 5 minutes.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 shows a flowchart for a method of preparing protein samples.

FIG. 10 shows the proteome as expected from Open-SWATH database, a proteomics repository, for comparison with the proteome as detected using the scheme in FIG. 8 with Data-Independent Analysis (Chromatin-DIA). The box-plot shows the more highly expressed genes result in higher peptide detection.

FIG. 12 shows transcription factors are extracted in the chromatin fraction associated with their known function.

DETAILED DESCRIPTION OF THE INVENTION

Figure 1:
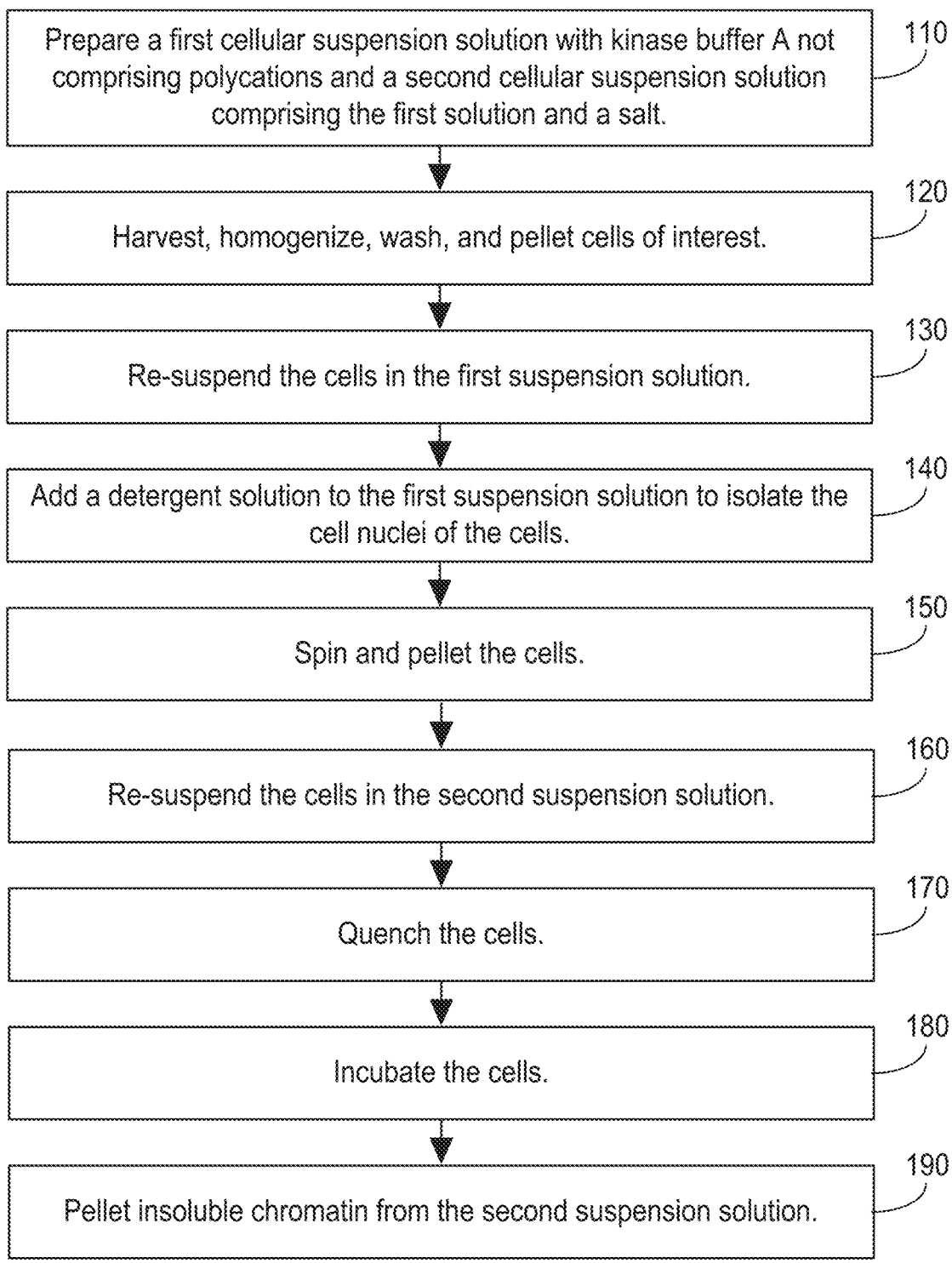
FIG. 1 shows a flowchart of a method for preparing cells.

The methods disclosed herein relate to solubilizing and isolating chromatin-associated protein complexes from cells. Regulatory DNA may be characterized by the cooperative binding of sequence-specific transcription factors (TFs) and their associated cofactors, chromatin remodelers, and modified histone proteins. Although catalogues of DNA sites harboring regulatory potential may be compiled using existing technologies, the protein compartment responsible for transcriptional regulation remains to be better and more comprehensively characterized. For example, currently, mRNA levels of these proteins may be used as a proxy for their abundance and activity. However, RNA-based measurements may not correlate highly with protein abundance and may not capture subcellular location or proteoform diversity. Previous attempts to assay proteins involved in transcriptional regulation have used isotope labelling schemes that are expensive, hamper sensitivity, limit reproducibility, and restrict the number of samples in a single analysis.

As disclosed in this application, a data-independent acquisition proteomics strategy that comprehensively samples the nuclear proteome for bottom-up proteomics may be used to target TFs and cofactors. For example, facile nuclear sub-fractionation approaches may be combined with label-free mass spectrometry to improve sensitivity and quantification of nuclear proteins in human cells and tissues. Nuclei may be isolated and subjected to a series of extraction conditions that enrich for nucleoplasm, euchromatin, heterochromain, and nuclear-membrane associated proteins. Proteomics measurements may then be made with a data-independent acquisition strategy and may be analyzed with peptide-centric analysis methods. These methods may be scalable to measure hundreds of conditions in a single experiment. These methods may be effective for a wide array of cell lines and primary human tissues.

The peptides identified using the methods as described herein may be assigned into functional chromatin compartments and may illuminate systems-wide nuclear protein dynamics. Chromatin compartments may be validated using established immunofluorescence databases and known function of chromatin-active protein complexes. By integrating with data available from various epigenomics consortia, more faithful transcriptional networks that include nuclear subcompartment information may be built using the methods as described herein.

Furthermore, disclosed herein is a technology that may be used for highly-parallel, reproducible, comprehensive characterization of the nuclear proteome and for observing systems-wide effects of pharmacological perturbation.

Samples of Interest

A sample described herein may be a fresh sample or a fixed sample. The sample may be a fresh sample. The sample may be a fixed sample. The sample may be subjected to a denaturing condition. The sample may be cryopreserved.

The sample may be a cell sample. The cell sample may be obtained from the cells of an animal. The animal cell may comprise a cell from a marine invertebrate, fish, insect, amphibian, reptile, or mammal. The mammalian cell may be obtained from a human, non-human primate, ape, equine, bovine, porcine, canine, feline, or rodent. The mammal may be a human, non-human primate, ape, dog, cat, rabbit, ferret, or the like. The rodent may be a mouse, rat, hamster, gerbil, hamster, chinchilla, or guinea pig. The bird cell may be from a canary, parakeet, or parrots. The reptile cell may be from a turtle, lizard, or snake. The fish cell may be from a tropical fish. For example, the fish cell may be from a zebrafish (such as *Danio rerio*). The worm cell may be from a nematode (such as *Caenorhabditis elegans*). The amphibian cell may be from a frog. The arthropod cell may be from a tarantula or hermit crab.

The cell sample may be obtained from a mammalian cell. For example, the mammalian cell may be an epithelial cell, connective tissue cell, hormone secreting cell, a nerve cell, a skeletal muscle cell, a blood cell, an immune system cell, or a stem cell.

A cell sample may be cells derived from a cell line. Exemplary cell lines include, but are not limited to, 293A cell line, 293FT cell line, 293F cell line, 293 H cell line, HEK 293 cell line, CHO DG44 cell line, CHO-S cell line, CHO-K1 cell line, Expi293F™ cell line, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cell line, FreeStyle™ CHO-S cell line, GripTite™ 293 MSR cell line, GS-CHO cell line, HepaRG™ cell line, T-REx™ Jurkat cell line, Per.C6 cell line, T-REx™-293 cell line, T-REx™-CHO cell line, T-REx™-HeLa cell line, NC-HIMT cell line, and PC12 cell line.

The cell sample may be obtained from cells of a primate. The primate may be a human, or a non-human primate. The cell sample may be obtained from a human. For example, the cell sample may comprise cells obtained from blood, urine, stool, saliva, lymph fluid, cerebrospinal fluid, synovial fluid, cystic fluid, ascites, pleural effusion, amniotic fluid, chorionic villus sample, vaginal fluid, interstitial fluid, buccal swab sample, sputum, bronchial lavage, Pap smear sample, or ocular fluid. The cell sample may comprise cells obtained from a blood sample, an aspirate sample, or a smear sample.

The cell sample may be a circulating tumor cell sample. A circulating tumor cell sample may comprise lymphoma cells, fetal cells, apoptotic cells, epithelia cells, endothelial cells, stem cells, progenitor cells, mesenchymal cells, osteoblast cells, osteocytes, hematopoietic stem cells, foam cells, adipose cells, transcervical cells, circulating cardiocytes, circulating fibrocytes, circulating cancer stem cells, circulating myocytes, circulating cells from a kidney, circulating cells from a gastrointestinal tract, circulating cells from a lung, circulating cells from reproductive organs, circulating cells from a central nervous system, circulating hepatic cells, circulating cells from a spleen, circulating cells from a thymus, circulating cells from a thyroid, circulating cells from an endocrine gland, circulating cells from a parathyroid, circulating cells from a pituitary, circulating cells from an adrenal gland, circulating cells from islets of Langerhans, circulating cells from a pancreas, circulating cells from a hypothalamus, circulating cells from prostate tissues, circulating cells from breast tissues, circulating cells from circulating retinal cells, circulating ophthalmic cells, circulating auditory cells, circulating epidermal cells, circulating cells from the urinary tract, or combinations thereof.

A cell sample may be a peripheral blood mononuclear cell sample.

A cell sample may comprise cancerous cells. The cancerous cells may from a cancer which may be a solid tumor or a hematologic malignancy. The cancerous cell sample may comprise cells obtained from a solid tumor. The solid tumor may include a sarcoma or a carcinoma. Exemplary sarcoma cell sample may include, but are not limited to, cell sample obtained from alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (WE), malignant fibrous histiocytoma (WE) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

Exemplary carcinoma cell samples may include, but are not limited to, cell samples obtained from an anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

The cancerous cell sample may comprise cells obtained from a hematologic malignancy. Hematologic malignancy may comprise a leukemia, a lymphoma, a myeloma, a non-Hodgkin's lymphoma, or a Hodgkin's lymphoma. The hematologic malignancy may be a T-cell based hematologic malignancy. The hematologic malignancy may be a B-cell based hematologic malignancy. Exemplary B-cell based hematologic malignancy may include, but are not limited to, chronic lymphocytic leukemia (CLL), small lymphocytic lymphoma (SLL), high risk CLL, a non-CLL/SLL lymphoma, prolymphocytic leukemia (PLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. Exemplary T-cell based hematologic malignancy may include, but are not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

A cell sample described herein may comprise a tumor cell line sample. Exemplary tumor cell line sample may include, but are not limited to, cell samples from tumor cell lines such as 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Ly1, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

A cell sample may comprise cells obtained from a biopsy sample.

The cell samples (such as a biopsy sample) may be obtained from an individual by any suitable means of obtaining the sample using well-known and routine clinical methods. Procedures for obtaining tissue samples from an individual are well known. For example, procedures for drawing and processing tissue sample such as from a needle aspiration biopsy are well-known and may be employed to obtain a sample for use in the methods provided. Typically, for collection of such a tissue sample, a thin hollow needle is inserted into a mass such as a tumor mass for sampling of cells that, after being stained, will be examined under a microscope.

Cell Isolation

FIG. 1 shows a flowchart of a method 100 for preparing cells.

In a first operation 110, the method may comprise preparing a first suspension solution and a second suspension solution. The first suspension solution may comprise buffer A. The buffer A may not comprise polycations such as spermidine or spermine. The buffer A may be prepared without the polycations. Alternatively, the polycations may be removed from the buffer A after preparation of buffer A. The operation 110 may comprise removing spermidine from the buffer A. The operation 110 may comprise removing spermine from the buffer A. The operation 110 may comprise preparing the buffer A with the absence of spermidine. The operation 110 may comprise preparing the buffer A with the absence of spermine.

The second suspension solution may comprise the first suspension solution and a salt. The salt may comprise an alkali or alkaline earth salt, such as a lithium salt, a sodium salt, a potassium salt, a rubidium salt, a magnesium salt, a calcium salt, or a strontium salt. The salt may comprise a halide salt, such as a fluoride salt, a chloride salt, a bromide salt, or an iodide salt. The salt may comprise an alkali halide salt, such as lithium fluoride, lithium chloride, lithium bromide, lithium iodide, sodium fluoride, sodium chloride, sodium bromide, sodium iodide, potassium fluoride, potassium chloride, potassium bromide, or potassium iodide. The salt may comprise an alkaline earth halide salt, such as magnesium fluoride, magnesium chloride, magnesium bromide, magnesium iodide, calcium fluoride, calcium chloride, calcium bromide, calcium iodide, strontium fluoride, strontium chloride, strontium bromide, or strontium iodide.

The salt may comprise an ammonium salt. The salt may comprise a transition metal salt. The salt may comprise an acetate, benzoate, carbonate, chromate, citrate, cyanide, hypochlorite, chlorite, chlorate, perchlorate, dichromate, dihydrogen phosphate, bicarbonate, bisulfate, hydrogen phosphate, hydroxide, nitrite, nitrate, peroxide, permanganate, phosphate, sulfite, or sulfate salt.

The salt may be present at a concentration of about 1 nM, 2.5 nM, 5 nM, 10 nM, 25 nM, 50 nM, 100 nM, 250 nM, 500 nM, 1 µM, 2.5 µM, 5 µM, 10 µM, 25 µM, 50 µM, 100 µM, 250 µM, 500 µM, or 1 mM. The salt may be present at a concentration that is within a range defined by any two of the preceding values.

In a second operation 120, the method may comprise one or more of harvesting, washing, or pelleting the cells of interest.

In a third operation 130, the method may comprise re-suspending the cells in the first suspension solution.

In a fourth operation 140, the method may comprise adding a detergent solution to the first suspension solution to isolate the cell nucleic of the cells. The detergent solution may be ionic or non-ionic. The detergent solution may comprise NP40 detergent solution. The detergent solution comprise SDS, TritonX100, or Tween20. The detergent solution may be a mass-spectrometry acid-labile detergent. The detergent solution may be added at a concentration from 0 to 4%. The detergent solution may be added at a concentration of from 0.01% to 0.1%.

In a fifth operation 150, the method may comprise spinning and pelleting the cells. The operation 150 may further comprise treating the cells with a micrococcal nuclease (MNase). The cells may be treated with an MNase at a temperature of about 0° C., about 10° C., about 20° C., about 30° C., about 37° C., about 40° C., or about 50° C. The cells may be treated with an MNase at a temperature that is within a range defined by any two of the preceding values. The cells may be treated with an MNase for a period of about 1 minute, about 2 minutes, about 5 minutes, about 10 minutes, about 20 minutes, about 50 minutes, or about 100 minutes. The cells may be treated with an MNase for a period that is within a range defined by any two of the preceding values.

In a sixth operation 160, the method may comprise re-suspending the cells in the second suspension solution.

In a seventh operation 170, the method may comprise quenching the cells. The operation 170 may comprise quenching the cells with ethylenediaminetetraacetic acid (EDTA). The operation 170 may comprise quenching the cells with egtazic acid (EGTA). The operation 170 may comprise quenching the cells with a final concentration of EDTA or EGTA of from 0.1 mM to 10 mM.

In an eighth operation 180, the method may comprise incubating the cells. The cells may be incubated at a temperature of about 0° C., about 4° C., about 10° C., about 20° C., about 40° C., or about 100° C. The cells may be incubated at a temperature that is within a range defined by any two of the preceding values. The cells may be incubated for a period of about 1 minute, about 3 minutes, about 5 minutes, about 10 minutes, about 30 minutes, about 50 minutes, or about 100 minutes. The cells may be incubated for a period that is within a range defined by any two of the preceding values.

In a ninth operation 190, the method may comprise pelleting insoluble chromatin from the second suspension solution. The pelleted insoluble chromatin may be saved for further analysis.

The method may further comprise collecting supernatant liquid from the second suspension solution. The supernatant liquid may be saved for further analysis. The supernatant liquid may be enriched in transcriptional regulators.

Protein Sample Preparation

FIG. 2 shows a flowchart for a method 200 of preparing protein samples.

In a first operation 210, the method may comprise collecting the pelleted chromatin generated in operation 190 of method 100.

In a second operation 220, the method may comprise adding a cleavable surfactant to the chromatin pellet to form a first solution. The cleavable surfactant may comprise sodium 3-(4-(1,1-bis(hexyloxy)ethyl))pyridinium-1yl)propane-1-sulfonate (PPS), sodium 3-((1-(furan-2-yl)undecyloxy)carbonylamino)propane-1-sulfonate (ProteaseMAX), or sodium 3-[(2-methyl-2-undecyl-1,3-dioxolan-4-yl)methoxy]-1-propanesulfonate (RapiGest SF). The operation 220 may comprise adding about 100 μL of cleavable surfactant, about 200 μL of cleavable surfactant, about 300 μL of cleavable surfactant, about 400 μL of cleavable surfactant, about 500 μL of cleavable surfactant, about 600 μL of cleavable surfactant, about 700 μL of cleavable surfactant, about 800 μL of cleavable surfactant, about 900 μL of cleavable surfactant, or about 1 mL of cleavable surfactant to the chromatin pellet. The operation 220 may comprise adding a volume of cleavable surfactant that is within a range defined by any two of the preceding values. The method may further comprise sonicating the first solution. The operation 220 may comprise sonicating the first solution for a period of about 1 second, about 3 seconds, about 5 seconds, about 10 seconds, about 30 seconds, about 50 seconds, or about 100 seconds. The operation 220 may comprise sonicating the first solution for a period that is within a range defined by any two of the preceding values. The operation 220 may comprise obtaining a protein concentration. For instance, the operation 220 may comprise obtaining an A280 reading.

In a third operation 230, the method may comprise heating the first solution. The operation 230 may comprise boiling the first solution. The operation 230 may comprise boiling the first solution for a period of about 1 minute, about 2 minutes, about 5 minutes, about 10 minutes, about 20 minutes, about 50 minutes, or about 100 minutes. The operation 230 may comprise boiling the first solution for a period of time that is within a range defined by any two of the preceding values. The operation 230 may comprise allowing the first solution to cool. The operation 230 may comprise spinning down the first solution.

In a fourth operation 240, the method may comprise adding a reducing agent to the first solution to obtain a second solution. The reducing agent may comprise dithiothreitol (DTT). The operation 240 may comprise adding reducing agent to obtain a final reducing agent concentration of about 1 mM, about 2 mM, about 5 mM, about 10 mM, about 20 mM, about 50 mM, or about 100 mM. The operation 240 may comprise adding reducing agent to obtain a final reducing agent concentration that is within a range defined by any two of the preceding values. The operation 240 may comprise allowing the second solution to incubate for a period of about 1 minute, about 2 minutes, about 5 minutes, about 10 minutes, about 20 minutes, about 30 minutes, about 50 minutes, about 1 hour, about 2 hours, about 5 hours, or about 10 hours. The second solution may be incubated at from 55° C. to 65° C., 58° C. to 63° C., 59° C. to 62° C., or 59° C. to 61° C. The reducing agent may be used at a concentration of 5 mM for 30 minutes at 60° C. DTT may be used at a concentration of 5 mM for 30 minutes at 60° C. The operation 240 may comprise allowing the second solution to sit for a period that is within a range defined by any two of the preceding values.

In a fifth operation 250, the method may comprise adding an alkylating agent to the second solution to obtain a third solution. The alkylating agent may comprise 2-iodoacetamide (IAA). IAA may be used at a final alkylating agent concentration of 15 mM. The operation 250 may comprise adding alkylating agent to obtain a final alkylating agent concentration of about 5 mM, about 10 mM, about 15 mM, about 20 mM, about 25 mM, about 30 mM, about 40 mM, about 45 mM, or about 50 mM. The operation 250 may comprise adding alkylating agent to obtain a final alkylating agent concentration that is within a range defined by any two of the preceding values. The operation 250 may comprise allowing the third solution to incubate for a period of about 1 minute, about 3 minutes, about 5 minutes, about 10 minutes, about 30 minutes, about 50 minutes, or about 100 minutes. The IAA may be incubated with the sample for 30 min. The operation 250 may comprise allowing the third solution to sit for a period that is within a range defined by any two of the preceding values. The operation 250 may comprise allowing the third solution to incubate in the dark. The operation 250 may comprise allowing the third solution to incubate at room temperature.

In a sixth operation 260, the method may comprise adding a trypsin-acetic acid mixture to the third solution to obtain a fourth solution. The trypsin-acetic acid mixture may be formed from a 0.01% acetic acid solution, a 0.02% acetic acid solution, a 0.05% acetic acid solution, a 0.1% acetic acid solution, a 0.2% acetic acid solution, a 0.5% acetic acid solution, or a 1% acetic acid solution. The trypsin-acetic acid may be formed from an acetic acid solution comprising acetic acid that is present at a concentration that is within a range defined by any two of the preceding values. The trypsin-acetic acid may be formed from 1 μL acetic acid solution, 2 μL acetic acid solution, 5 μL acetic acid solution, 10 μL acetic acid solution, 20 μL acetic acid solution, 50 μL acetic acid solution, 100 μL acetic acid solution, 200 μL acetic acid solution, 500 μL acetic acid solution, or 1 mL acetic acid solution. The trypsin-acetic acid may be formed for an acetic acid solution having a volume that is within a range defined by any two of the preceding values. The trypsin-acetic acid mixture may be formed from trypsin that is present at a concentration of about 100 ng/μL, about 200 ng/μL, about 500 ng/μL, or about 1 μg/μL. The trypsin-acetic acid mixture may be formed from trypsin that is present at a concentration that is within a range defined by any two of the preceding values. The trypsin-acetic acid mixture may be added to the third solution to obtain a final protein:trypsin concentration of about 1:1, about 2:1, about 5:1, about 10:1, about 20:1, about 50:1, or about 100:1. The trypsin-acetic acid mixture may be added to the third solution to obtain a final protein:trypsin concentration that is within a range defined by any two of the preceding values. The operation 260 may comprise incubating the fourth solution. The fourth solution may be incubated at about 0° C., about 10° C., about 20° C., about 30° C., about 37° C., about 40° C., or about 50° C. The fourth solution may be incubated at a temperature that is within a range defined by any two of the preceding values. The fourth solution may be incubated for a period of about 1 minute, about 2 minutes, about 5 minutes, about 10 minutes, about 20 minutes, about 50 minutes, about 1 hour, about 2 hours, about 5 hours, or about 10 hours. The fourth solution may be incubated for a period that is within a range defined by any two of the preceding values.

In a seventh operation 270, the method may comprise adding a strong acid to the fourth solution to obtain a fifth solution. The strong acid may comprise hydrochloric acid (HCl). The strong acid may be added to obtain a pH of at most 5, at most 4, at most 3, at most 2, or at most 1. The strong acid may be added to obtain a pH that is within a range defined by any two of the preceding values. The operation 270 may comprise allowing the fifth solution to sit for a period of about 1 minute, about 2 minutes, about 5 minutes, about 10 minutes, about 20 minutes, about 50 minutes, or about 100 minutes. The operation 270 may comprise allowing the fifth solution to sit for a period that is within a range defined by any two of the preceding values. The operation 270 may comprise spinning the fifth solution at a rotational speed of about 1,000 rpm, about 1,500 rpm, about 2,000 rpm, about 5,000 rpm, about 10,000 rpm, about 15,000 rpm, or about 20,000 rpm. The operation 270 may comprise spinning the fifth solution at a rotational speed that is within a range defined by any two of the preceding values. The operation 270 may comprise spinning the fifth solution for a period of about 1 minute, about 2 minutes, about 5 minutes, about 10 minutes, about 20 minutes, about 50 minutes, or about 100 minutes. The operation 270 may comprise spinning the fifth solution for a period that is within a range defined by any two of the preceding values. The operation 270 may comprise spinning the fifth solution at a temperature of about 0° C., about 2° C., about 4° C., about 10° C., about 20° C., or about 40° C. The operation 270 may comprise spinning the fifth solution at a temperature that is within a range defined by any two of the preceding values.

In an eighth operation 280, the method may comprise cleaning up the fifth solution. The fifth solution may be cleaned up using a chromatographic cartridge. The fifth solution may be cleaned up using a solid-phase chromatographic cartridge. The fifth solution may be cleaned up using a solid-phase microextraction (SPME) chromatographic cartridge. The fifth solution may be cleaned up using a MCX cartridge. The fifth solution may be cleaned up using dialysis. The fifth solution may be cleaned up using ion exchange.

Figure 8:
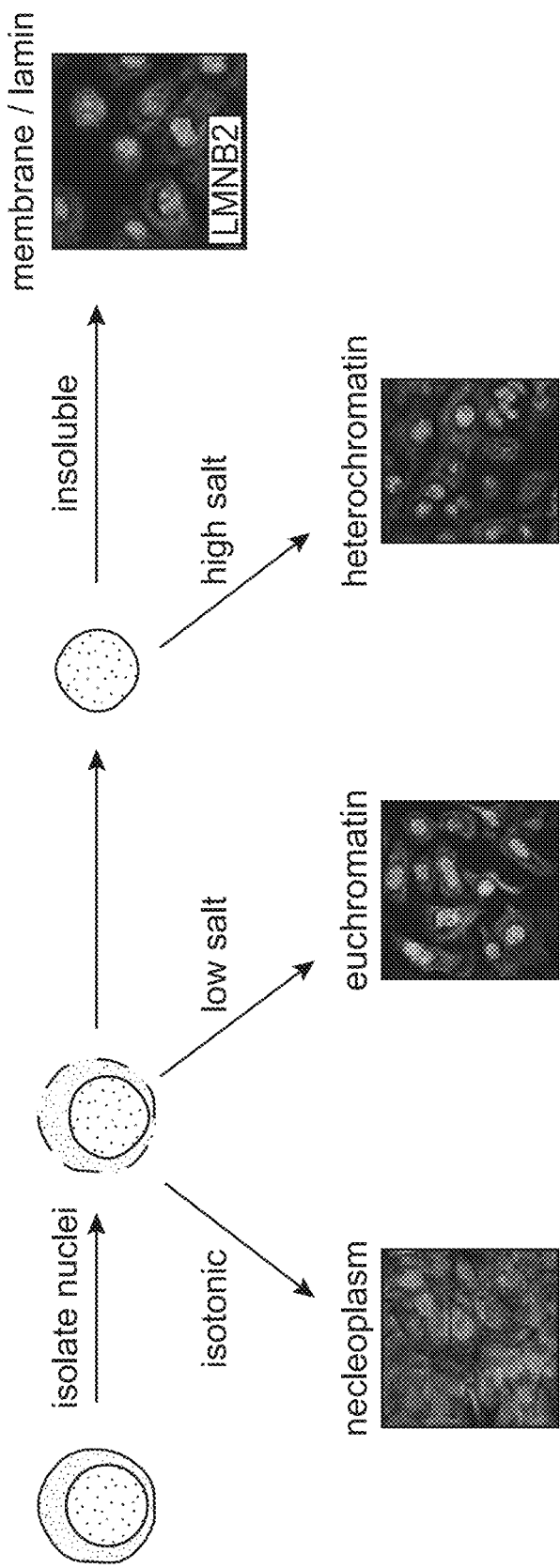
FIG. 8 shows a scheme for nuclei isolated and subjected to a series of extraction conditions that enrich for nucleoplasm, euchromatin, heterochromain, and nuclear-membrane associated proteins.

FIG. 8 shows an exemplary scheme for nuclei isolated and subjected to a series of extraction conditions that enrich for nucleoplasm, euchromatin, heterochromain, and nuclear-membrane associated proteins using the methods as described above.

Data Acquisition

Figure 3:
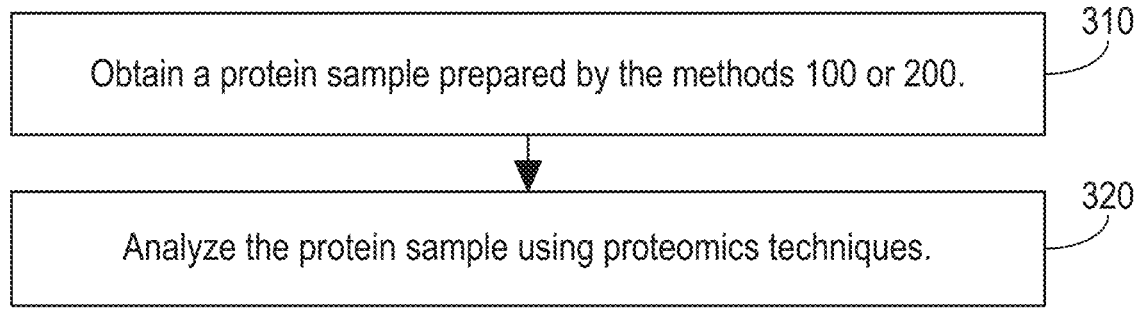
FIG. 3 shows a flowchart for a method of analyzing protein samples.

FIG. 3 shows a flowchart for a method 300 of analyzing protein samples.

In a first operation 310, the method may comprise obtaining a protein sample prepared by the methods 100 and/or 200.

In a second operation 320, the method may comprise analyzing the protein sample using proteomics techniques. For instance, the samples may be analyzed using mass spectrometry (MS), such as tandem mass spectrometry (MS-MS), time-of-flight mass spectrometry (TOF-MS), quadrupole mass spectrometry (Q-MS), or any combination thereof. The samples may be analyzed using a combination of chromatographic and mass spectrometric techniques, such as gas chromatography-mass spectrometry (GC-MS), liquid chromatography-mass spectrometry (LC-MS), or high pressure liquid chromatography-mass spectrometry (HPLC-MS).

Many variations, alterations, and adaptations based on the methods 100, 200, or 300 provided herein are possible. For example, the order of the operations of the methods 100, 200, or 300 may be changed, some of the operations removed, some of the operations duplicated, and additional operations added as appropriate. Some of the operations may be performed in succession. Some of the operations may be performed in parallel. Some of the operations may be performed once. Some of the operations may be performed more than once. Some of the operations may comprise sub-operations. Some of the operations may be automated and some of the operations may be manual.

The methods described herein, such as methods 100, 200, or 300, may be used to enhance mass spectrometry signals obtained from chromatin-binding proteins.

The methods described herein, such as methods 100, 200, or 300, may be used to compare nuclear proteomes across two or more conditions. For instance, the methods described herein, such as methods 100, 200, or 300, may be used to characterize nuclear proteome changes in response to one or more external perturbations. Such perturbations may include, but are not limited to, a change in cell state, cell environment, or exposure of the cell to a chemical treatment or physical stress.

The methods described herein, such as methods 100, 200, or 300, may be used to characterize small molecule degradation compounds. Small molecule degradation is a promising new therapeutic strategy for selective tagging of a protein target for proteasomal degradation. The methods described herein, such as methods 100, 200, or 300, may be used to screen small molecule degraders in an unbiased manner to identify proteins targeted for degradation in response to treatment.

The methods described herein, such as methods 100, 200, or 300, may be used to assay cellular thermal shifts. The assay may detect compound engagement with the protein target in living cells by measuring changes in thermal stability of the protein. The methods described herein, such as methods 100, 200, or 300, may be used to profile thermal stability of the nuclear proteome and to study compounds interacting with nuclear proteins.

The methods described herein, such as methods 100, 200, or 300, may be used to characterize genome edits. Genome editing with clustered regularly interspersed palindromic repeats (CRISPR)-based genome editing techniques, transcription activator-like effector nuclear (TALEN)-based genome editing techniques, zinc finger-based genome editing techniques, or other nuclease technologies can create mutations in the DNA of a cell. These mutations may result in global changes in the proteome and/or the nuclear proteome which may be detected with the methods described herein, such as methods 100, 200, or 300.

Digital Processing Device

The systems, apparatus, and methods described herein may include a digital processing device, or use of the same. The digital processing device may include one or more hardware central processing units (CPU) that carry out the device's functions. The digital processing device may further comprise an operating system configured to perform executable instructions. In some instances, the digital processing device is connected to a computer network, is connected to the Internet such that it accesses the World Wide Web, and/or is connected to a cloud computing infrastructure. In some instances, the digital processing device is connected to an intranet. In some instances, the digital processing device is connected to a data storage device.

In accordance with the description herein, suitable digital processing device may include, by way of non-limiting examples, a server computer, a desktop computer, a laptop computer, a notebook computer, a sub-notebook computer, a netbook computer, a netpad computer, a set-top computer, a media streaming device, a handheld computer, an Internet appliance, a mobile smartphone, a tablet computer, a personal digital assistant, a video game console, and a vehicle. Those of skill in the art will recognize that many smartphones may be suitable for use in the system described herein. Those of skill in the art will also recognize that select televisions, video players, and digital music players with optional computer network connectivity may be suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which may manage the device's hardware and provides services for execution of applications. Those of skill in the art will recognize that suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some cases, the operating system is provided by cloud computing. Those of skill in the art will also recognize that suitable mobile smart phone operating systems may include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems may include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems may include, by way of non-limiting examples, Sony® PS3®, Sony® PS4®, Microsoft® Xbox 360®, Microsoft Xbox One, Nintendo® Wii®, Nintendo® Wii U®, and Ouya®.

In some instances, the device may include a storage and/or memory device. The storage and/or memory device may be one or more physical apparatuses used to store data or programs on a temporary or permanent basis. In some instances, the device is volatile memory and requires power to maintain stored information. In other instances, the device is non-volatile memory and retains stored information when the digital processing device is not powered. In still other instances, the non-volatile memory comprises flash memory. The non-volatile memory may comprise dynamic random-access memory (DRAM). The non-volatile memory may comprise ferroelectric random access memory (FRAM). The non-volatile memory may comprise phase-change random access memory (PRAM). The device may be a storage device including, by way of non-limiting examples, CD-ROMs, DVDs, flash memory devices, magnetic disk drives, magnetic tapes drives, optical disk drives, and cloud computing based storage. The storage and/or memory device may also be a combination of devices such as those disclosed herein.

The digital processing device may include a display to send visual information to a user. The display may be a cathode ray tube (CRT). The display may be a liquid crystal display (LCD). Alternatively, the display may be a thin film transistor liquid crystal display (TFT-LCD). The display may further be an organic light emitting diode (OLED) display. In various cases, on OLED display is a passive-matrix OLED (PMOLED) or active-matrix OLED (AMO-LED) display. The display may be a plasma display. The display may be a video projector. The display may be a combination of devices such as those disclosed herein.

The digital processing device may also include an input device to receive information from a user. For example, the input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. Alternatively, the input device may be a Kinect™, Leap Motion™, or the like. In further aspects, the input device may be a combination of devices such as those disclosed herein.

Non-Transitory Computer Readable Storage Medium

In some instances, the systems, apparatus, and methods disclosed herein may include one or more non-transitory computer readable storage media encoded with a program including instructions executable by the operating system of an optionally networked digital processing device. In further instances, a computer readable storage medium is a tangible component of a digital processing device. In still further instances, a computer readable storage medium may be removable from a digital processing device. A computer readable storage medium may include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

The systems, apparatus, and methods disclosed herein may include at least one computer program, or use of the same. A computer program may include a sequence of instructions, executable in the digital processing device's CPU, and written to perform a specified task. In some embodiments, computer readable instructions are implemented as program modules, such as functions, objects, Application Programming Interfaces (APIs), data structures, and the like, that perform particular tasks or implement particular abstract data types. In light of the disclosure provided herein, those of skill in the art will recognize that a computer program, in certain embodiments, may be written in various versions of various languages.

The functionality of the computer readable instructions may be combined or distributed as desired in various environments. A computer program may comprise one sequence of instructions. A computer program may comprise a plurality of sequences of instructions. In some instances, a computer program is provided from one location. In other instances, a computer program is provided from a plurality of locations. In additional cases, a computer program includes one or more software modules. Sometimes, a computer program may include, in part or in whole, one or more web applications, one or more mobile applications, one or more standalone applications, one or more web browser plug-ins, extensions, add-ins, or add-ons, or combinations thereof.

Web Application

A computer program may include a web application. In light of the disclosure provided herein, those of skill in the art will recognize that a web application, in various aspects, may utilize one or more software frameworks and one or more database systems. In some cases, a web application is created upon a software framework such as Microsoft® .NET or Ruby on Rails (RoR). In some cases, a web application utilizes one or more database systems including, by way of non-limiting examples, relational, non-relational, object oriented, associative, and XML database systems. Sometimes, suitable relational database systems may include, by way of non-limiting examples, Microsoft® SQL Server, mySQL™, and Oracle®. Those of skill in the art will also recognize that a web application, in various instances, may be written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. Sometimes, a web application may be written to some extent in a database query language such as Structured Query Language (SQL). Other times, a web application may integrate enterprise server products such as IBM® Lotus Domino®. In some instances, a web application includes a media player element. In various further instances, a media player element utilizes one or more of many suitable multimedia technologies including, by way of non-limiting examples, Adobe® Flash®, HTML 5, Apple® QuickTime®, Microsoft® Silverlight®, Java™, and Unity®.

Mobile Application

A computer program may include a mobile application provided to a mobile digital processing device. In some cases, the mobile application is provided to a mobile digital processing device at the time it is manufactured. In other cases, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications may be written in several languages. Suitable programming languages may include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments may include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost, which may include, by way of non-limiting examples, Lazarus, MobiFlex, MoSync, and Phonegap. Also, mobile device manufacturers may distribute software developer kits, which may include, by way of non-limiting examples, iPhone and iPad (iOS) SDK, Android™ SDK, BlackBerry SDK, BREW SDK, Palm OS SDK, Symbian SDK, webOS SDK, and Windows® Mobile SDK.

Those of skill in the art will recognize that several commercial forums may be available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may include a standalone application, which is a program that is run as an independent computer process, not an add-on to an existing process, e.g., not a plug-in. Those of skill in the art will recognize that standalone applications may be compiled. A compiler is a computer program(s) that transforms source code written in a programming language into binary object code such as assembly language or machine code. Suitable compiled programming languages may include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. A computer program may include one or more executable complied applications.

Web Browser Plug-In

The computer program may include a web browser plug-in. In computing, a plug-in is one or more software components that add specific functionality to a larger software application. Makers of software applications support plug-ins to enable third-party developers to create abilities which may extend an application, may support easily adding new features, and may reduce the size of an application. When supported, plug-ins may enable customizing the functionality of a software application. For example, plug-ins may be used in web browsers to play video, generate interactivity, scan for viruses, and display particular file types. Those of skill in the art will be familiar with several web browser plug-ins, which may include Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that may enable development of plug-ins in various programming languages, including, by way of non-limiting examples, C++, Delphi, Java™ PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) may be designed for use on mobile digital processing devices, which may include, by way of non-limiting examples, handheld computers, tablet computers, netbook computers, subnotebook computers, smartphones, music players, personal digital assistants (PDAs), and handheld video game systems. Suitable mobile web browsers may include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The systems and methods disclosed herein may include software, server, and/or database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. In various aspects, the one or more software modules comprise, by way of non-limiting examples, a web application, a mobile application, and a standalone application. In some instances, software modules are in one computer program or application. In other instances, software modules are in more than one computer program or application. In some cases, software modules are hosted on one machine. In other cases, software modules are hosted on more than one machine. Sometimes, software modules may be hosted on cloud computing platforms. Other times, software modules may be hosted on one or more machines in one location. In additional cases, software modules are hosted on one or more machines in more than one location.

Databases

The methods, apparatus, and systems disclosed herein may include one or more databases, or use of the same. In view of the disclosure provided herein, those of skill in the art will recognize that many databases may be suitable for storage and retrieval of analytical information described elsewhere herein. In various aspects described herein, suitable databases may include, by way of non-limiting examples, relational databases, non-relational databases, object oriented databases, object databases, entity-relationship model databases, associative databases, and XML databases. A database may be internet-based. A database may be web-based. A database may be cloud computing-based. Alternatively, a database may be based on one or more local computer storage devices.

Services

Methods and systems described herein may further be performed as a service. For example, a service provider may obtain a sample that a customer wishes to analyze. The service provider may then encode the sample to be analyzed by any of the methods described herein, and may perform the analysis and provide a report to the customer. The customer may also perform the analysis and provide the results to the service provider for decoding. In some instances, the service provider then provides the decoded results to the customer. In other instances, the customer may receive encoded analysis of the samples from the provider and may decode the results by interacting with software installed locally (at the customer's location) or remotely (e.g., on a server reachable through a network). Sometimes, the software may generate a report and transmit the report to the costumer. Exemplary customers may include clinical laboratories, hospitals, industrial manufacturers, and the like. Sometimes, a customer or party may be any suitable customer or party with a need or desire to use the methods provided herein.

Server

Figure 4:
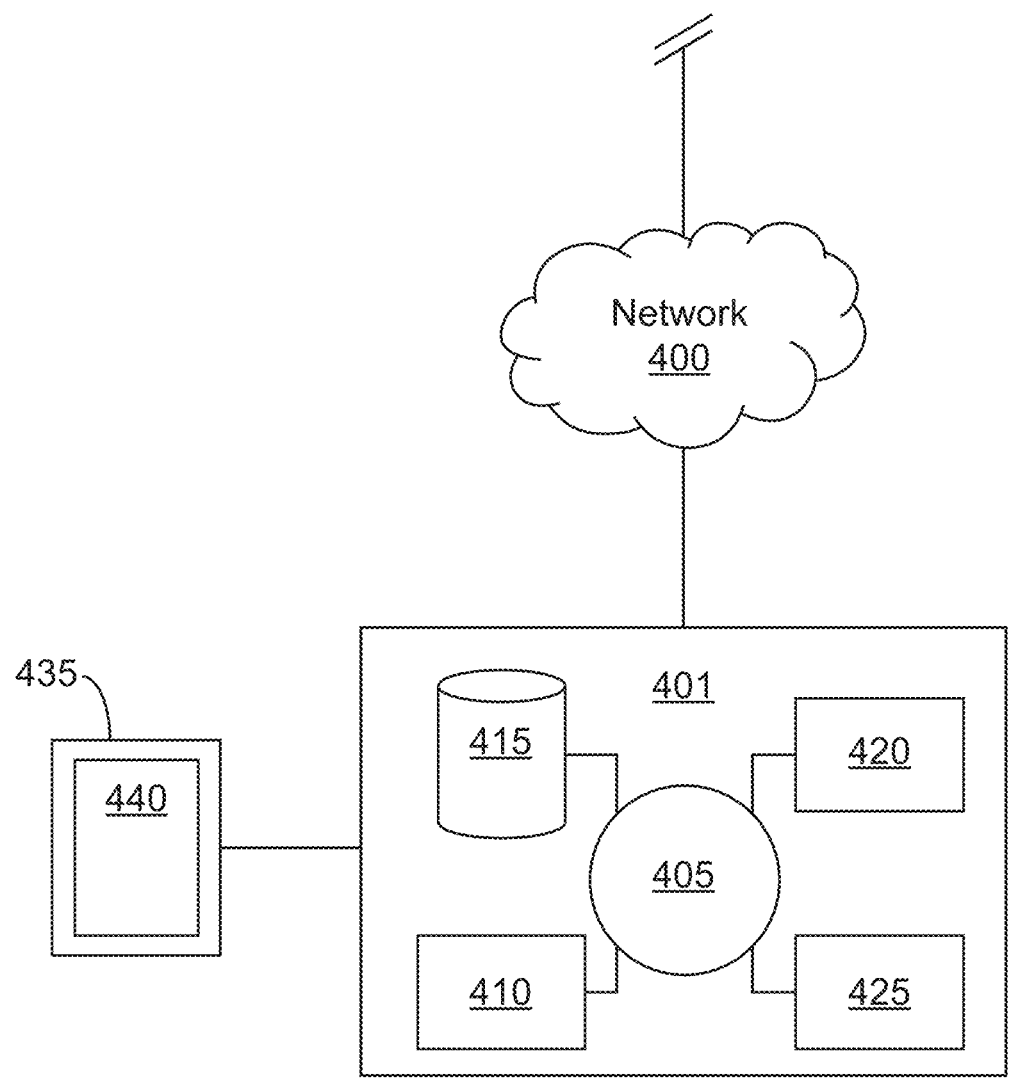
FIG. 4 shows a conceptual schematic of an exemplary computer server to be used for processing one or more methods described herein.

The methods provided herein may be processed on a server or a computer server, as shown in FIG. 4). The server 401 may include a central processing unit (CPU, also "processor") 405 which may be a single core processor, a multi core processor, or plurality of processors for parallel processing. A processor used as part of a control assembly may be a microprocessor. The server 401 may also include memory 410 (e.g., random access memory, read-only memory, flash memory); electronic storage unit 415 (e.g., hard disk); communications interface 420 (e.g., network adaptor) for communicating with one or more other systems; and peripheral devices 425 which includes cache, other memory, data storage, and/or electronic display adaptors. The memory 410, storage unit 415, interface 420, and peripheral devices 425 may be in communication with the processor 405 through a communications bus (solid lines), such as a motherboard. The storage unit 415 may be a data storage unit for storing data. The server 401 may be operatively coupled to a computer network ("network") 430 with the aid of the communications interface 420. A processor with the aid of additional hardware may also be operatively coupled to a network. The network 430 may be the Internet, an intranet and/or an extranet, an intranet and/or extranet that is in communication with the Internet, a telecommunication or data network. The network 430 with the aid of the server 401, may implement a peer-to-peer network, which may enable devices coupled to the server 401 to behave as a client or a server. The server may be capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 430. Moreover, a network may be used, for example, to transmit or receive data across an international border.

The server 401 may be in communication with one or more output devices 435 such as a display or printer, and/or with one or more input devices 440 such as, for example, a keyboard, mouse, or joystick. The display may be a touch screen display, in which case it functions as both a display device and an input device. Different and/or additional input devices may be present such as an enunciator, a speaker, or a microphone. The server may use any one of a variety of operating systems, such as for example, any one of several versions of Windows®, or of MacOS®, or of Unix®, or of Linux®.

The storage unit 415 may store files or data associated with the operation of a device, systems or methods described herein.

The server may communicate with one or more remote computer systems through the network 430. The one or more remote computer systems may include, for example, personal computers, laptops, tablets, telephones, Smart phones, or personal digital assistants.

A control assembly may include a single server 401. In other situations, the system may include multiple servers in communication with one another through an intranet, extranet, and/or the Internet.

The server 401 may be adapted to store device operation parameters, protocols, methods described herein, and other information of potential relevance. Such information may be stored on the storage unit 415 or the server 401 and such data may be transmitted through a network.

Methods of Use

The methods as described herein may be used for various different analyses involving the nuclear proteome. For example, these methods may be used for comparisons of nuclear proteomes across two conditions. The methods described herein may be used to characterize nuclear proteome changes in response to an external perturbation. For example, this perturbation may be a change in cell state, environment, or chemical or drug treatment.

These methods may be used for the characterization of small molecule degradation compounds. Small molecule degradation is a promising new therapeutic strategy for selective tagging of a protein target for proteasomal degradation. Cells treated with small molecule degraders may be screened using the methods described herein in an unbiased manner to identify proteins targeted for degradation in response to treatment.

These methods may be used to assess CETSA (Cellular thermal shift assay). This assay may detect compound engagement with its protein target in living cells by measuring changes in thermal stability of the protein. The methods described herein may be used to profile thermal stability of the nuclear proteome and may be used as a tool to study compounds interacting with nuclear proteins.

These methods may be used for the characterization of genome editing. Genome editing with CRISPR, TALENs, or other nuclease technology may create mutations in the DNA of a cell. These mutations may result in global changes in the nuclear proteome which may be detected using the methods described herein.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts may be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

While preferred embodiments of the present invention have been shown and described herein, it will be apparent to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

These examples are provided for illustrative purposes only and not to limit the scope of the claims provided herein.

Example 1

Chromatin Fractions

This example shows an overview of the chromatin fractions extracted from isolated nuclei. First, cells of interest are isolated. This is done by harvesting, homogenizing, washing, and then pelleting the cells of interest. The pellet is then resuspended in a buffer A not comprising polycations (e.g., no spermidine or spermine). NP40 detergent solution is then added to isolate nuclei and cells are spun and are pelleted. Optionally, prior to salt extraction, the pellet is treated with MNase at 37° C. for 5 minutes and is quenched with EDTA. The pellet is resuspended in buffer A and 250 nM NaCl, and then is incubated at 4° C. for 30 minutes. The insoluble chromatin is pelleted for later analysis. The supernatant is used for further analysis.

FIG. 8 shows a scheme for nuclei isolated and subjected to a series of extraction conditions that enrich for nucleoplasm, euchromatin, heterochromain, and nuclear-membrane associated proteins. The nucleoplasm associated proteins are extracted in an isotonic fraction. The euchromatin associated proteins are extracted in a low salt fraction. The heterochromatin associated proteins are extracted in a high salt fraction. The membrane/lamin associated proteins are extracted in an insoluble fraction.

Example 2

Protein Sample Preparation

This example shows a procedure for protein sample preparation. 400 ul of 01.% PPS is added to the nuclear pellet of EXAMPLE 1, which is then sonicated at a setting output of 5 for 30 seconds and a protein concentration is determined using A280 reading. The sample is then boiled at 99 C for 5 minutes, is allowed to cool at room temperature, and is then briefly spun down. DTT is added for a final concentration of 5 mM, and is incubated at 60° C. for 30 minutes. Next, IAA is added for a final concentration of 15 mM, and is incubated at room temperature in the dark for 30 minutes. 100 ul of 0.01% acetic acid is added to one vial of trypsin (200 ng/ul), and then tryspin is added for a final concentration of 1:50 enzyme:protein and is incubated at 37° C., shaking, for 2 hours. 5 ul of 5M HCl is added to the sample to obtain a pH of less than 3.0 and is incubated at room temperature for at least 20 minutes. The sample is then spun at 14,000 rpm for 10 minutes at 4° C., and then is cleaned up using MCX cartridge.

Example 3

Data Acquisition Procedure

This example shows a procedure for data acquisition. Data were acquired on a ThermoFisher QExactive-HF instrument operating in DIA mode. Reverse-phase liquid chromatography using an acetonitrile-water mixture was performed on a Waters nanoLC system with a flow rate of 0.3 µL/min. A custom hand-packed column containing 30 cm of C18 resin was used for chromatographic separation. 4 cm of C18 resin was used as a trap prior to chromatography. For library construction, overlapping 12 m/z DIA windows were collected over a mass range from 400-1,000 m/z in six separate runs. For sample measurement, overlapping 24 m/z DIA windows were collected over a mass range from 400-1,000 m/z in a single run. RAW files were converted to MZML with MSConvert software. Peptide identification and library construction was performed using PECAN software. Peptide quantification was performed using EncyclopeDIA software.

Example 4

Comparison of Data Dependent Acquisition and Data Independent Acquisition

Figure 5:
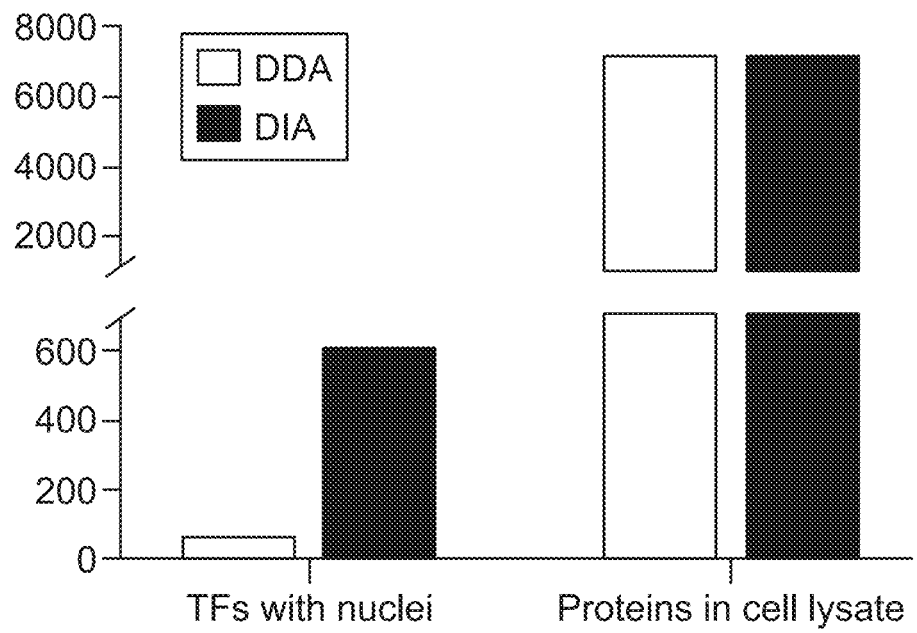
FIG. 5 shows the number of peptides acquired in different cellular fractions with data dependent acquisition and data independent acquisition (DIA).

FIG. 5 shows the number of peptides acquired in different cellular fractions with data dependent acquisition and data independent acquisition (DIA). As shown in FIG. 5, DIA allows detection of a substantially higher number of peptides.

Example 5

Limit of Detection

Figure 6:
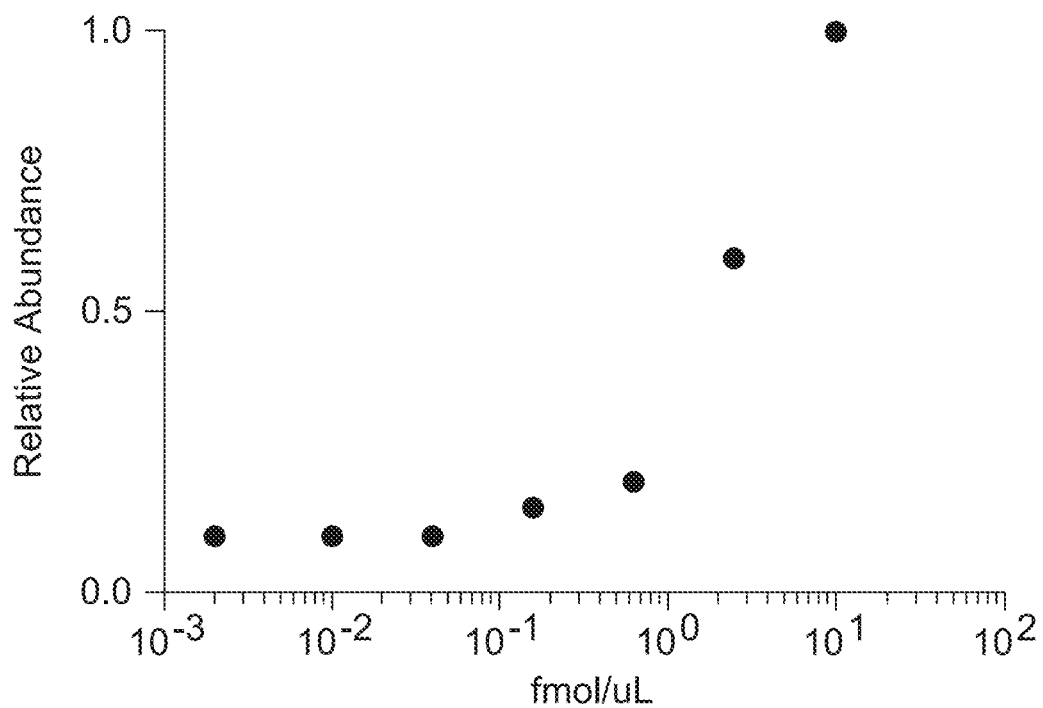
FIG. 6 shows a limit of detection of a nuclear isolate using DIA techniques.

FIG. 6 shows the limit of detection of a nuclear isolate using DIA techniques. As shown in FIG. 6, the methods described herein allow a limit of detection of approximately $10^8$ molecules for the nuclear isolate.

Example 6

Effect of Spermidine Removal

Figure 7:
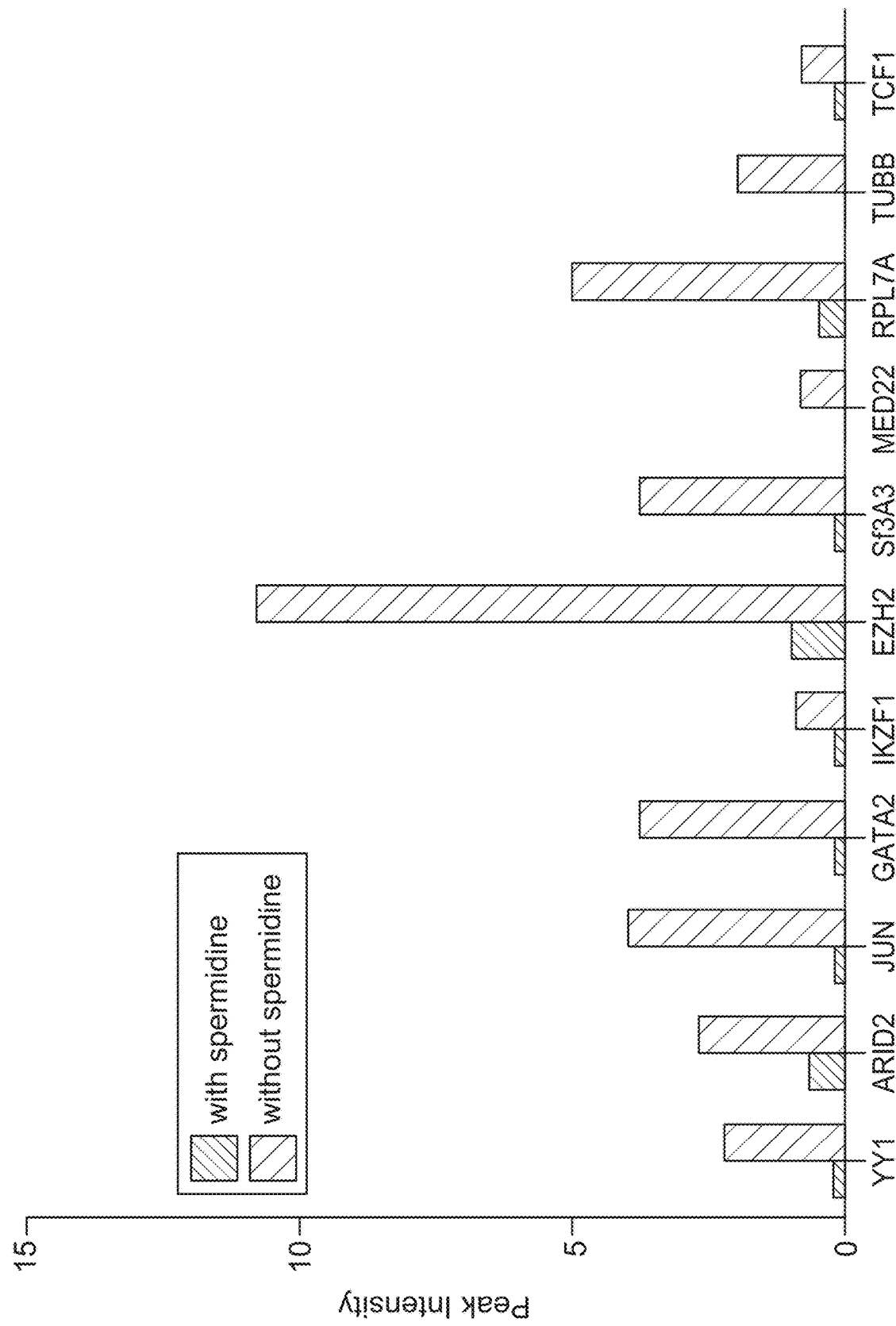
FIG. 7 shows the effect of spermidine removal on mass spectrometry peak intensity for selected genes of interest.

FIG. 7 shows the effect of spermidine removal on mass spectrometry peak intensity for selected genes of interest. As shown in FIG. 7, the removal of spermidine significantly enhances the mass spectrometry signal for all genes of interest.

Example 7

Transcription Factors in Chromatin Fractions

Figure 9:
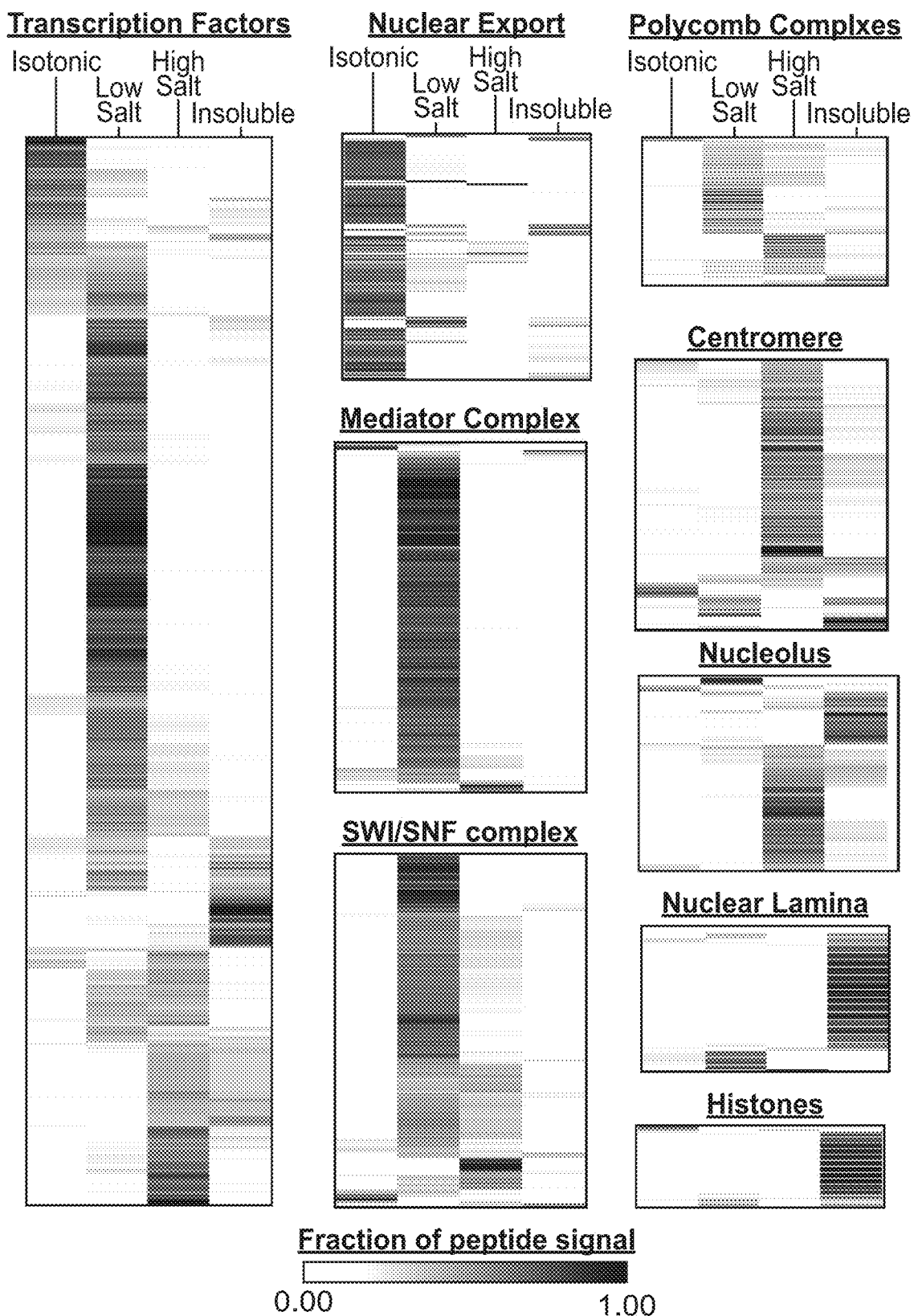
FIG. 9 shows a heat map of transcription factors. The heat map on the left is a heat map of all the transcription factors isolated according to the scheme in FIG. 8. The transcription factor heat maps in the middle and on the right are further grouped according to known function of the transcription factors, such as being associated with nuclear transport, the mediator complex, the SWI/SNF complex, polycomb complexes, the centromere, the nucleolus, the nuclear lamina, or histones. As expected, transcription factors associated with the nucleoplasm were mainly found in the isotonic fraction, transcription factors associated with euchromatin were mainly found in the low salt fraction, transcription factors associated with heterochromatin were mainly found in the high salt fraction, and transcription factors associated with the membrane/lamin were mainly found in the insoluble fraction.

This example shows the measurement peptides of over 70% of the expressed nuclear proteome. Nuclei were isolated and subjected to a series of extraction conditions that enrich for nucleoplasm, euchromatin, heterochromain, and nuclear-membrane associated proteins according to the scheme shown in FIG. 8. The nucleoplasm associated proteins were extracted in an isotonic fraction. The euchromatin associated proteins were extracted in a low salt fraction. The heterochromatin associated proteins were extracted in a high salt fraction. The membrane/lamin associated proteins were extracted in an insoluble fraction. FIG. 9 shows a heat map of the transcription factors extracted from the different chromatin fractions. The heat map on the left is a heat map of all the isolated transcription factors. The transcription factor heat maps in the middle and on the right are further grouped according to known function of the transcription factors, such as being associated with nuclear transport, the mediator complex, the SWI/SNF complex, polycomb complexes, the centromere, the nucleolus, the nuclear lamina, or histones. As expected, transcription factors associated with the nucleoplasm were mainly found in the isotonic fraction, transcription factors associated with euchromatin were mainly found in the low salt fraction, transcription factors associated with heterochromatin were mainly found in the high salt fraction, and transcription factors associated with the membrane/lamin were mainly found in the insoluble fraction.

FIG. 10 shows the proteome as expected from Open-SWATH database, a proteomics repository, for comparison with the proteome as detected using the scheme in FIG. 8 with Data-Independent Analysis (Chromatin-DIA). The box-plot shows the more highly expressed genes result in higher peptide detection.

Figure 11:
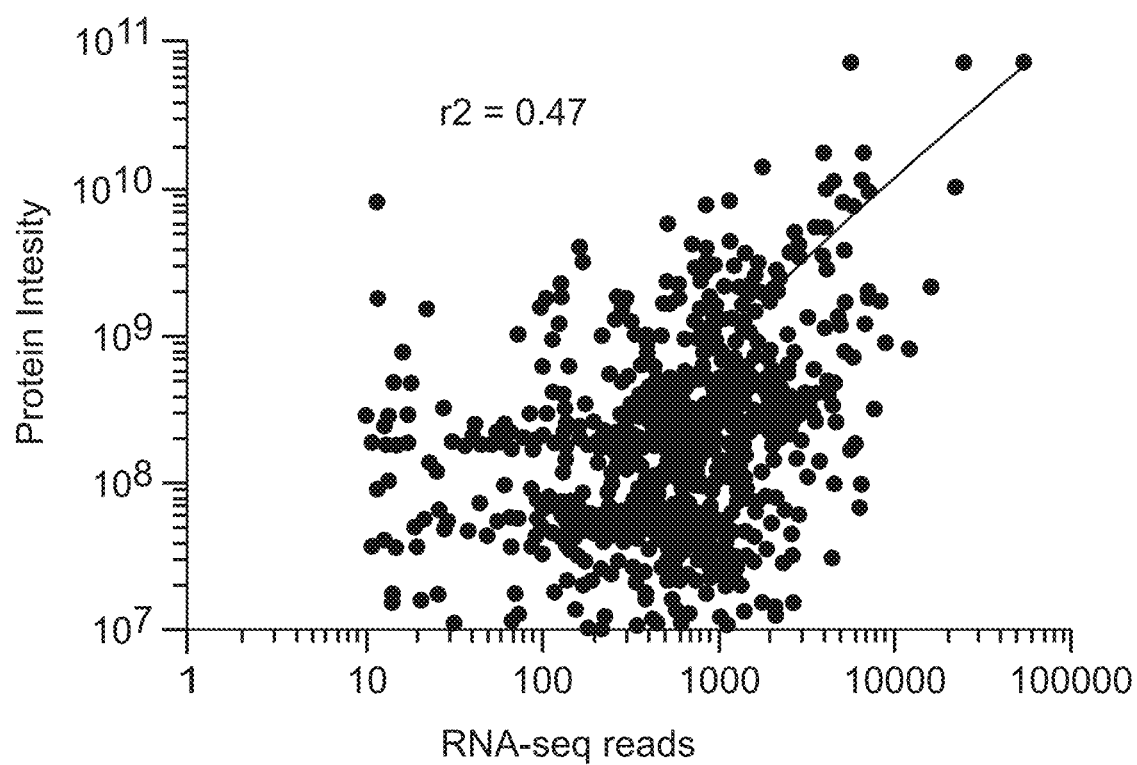
FIG. 11 shows the enrichment for classes of proteins with known nuclear function and depletion of classes of proteins with known non-nuclear function.

FIG. 11 shows the enrichment for classes of proteins with known nuclear function and depletion of classes of proteins with known non-nuclear function.

Example 8

Transcription Factors in Chromatin Fractions

Figure 12A:
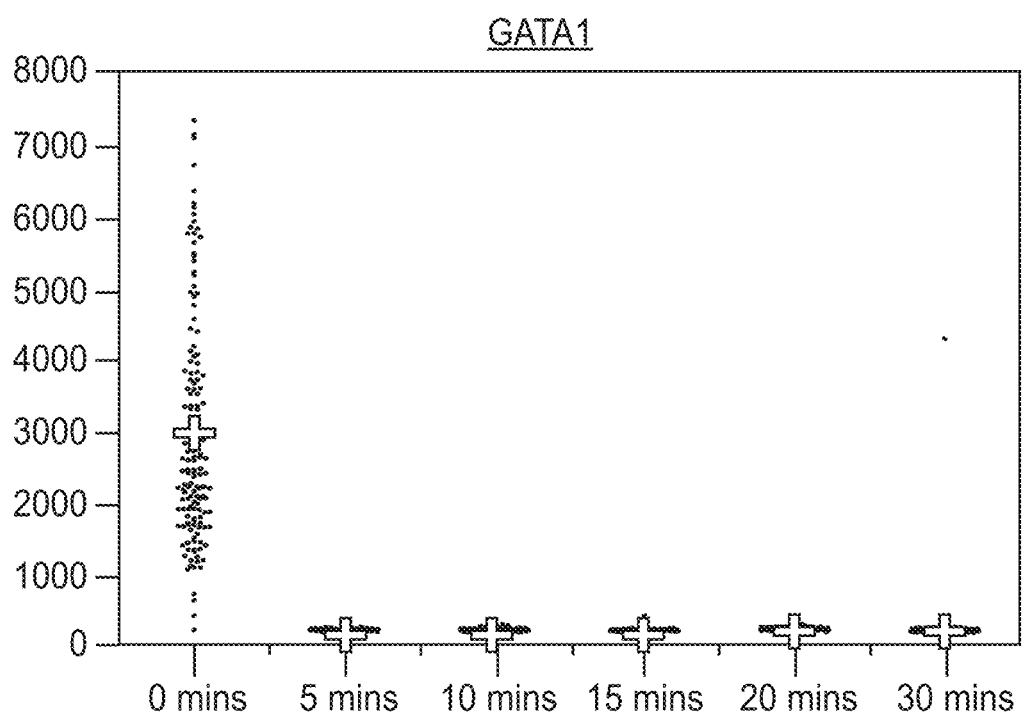
FIG. 12A shows immunofluorescence of the nucleus (DAPI), acetylated histones (H3K27ac), and euchromatin transcription factor (GATA1) during euchromatin extraction. GATA1 was completely extracted while H3K27ac remained in the nucleus.
Figure 12B:
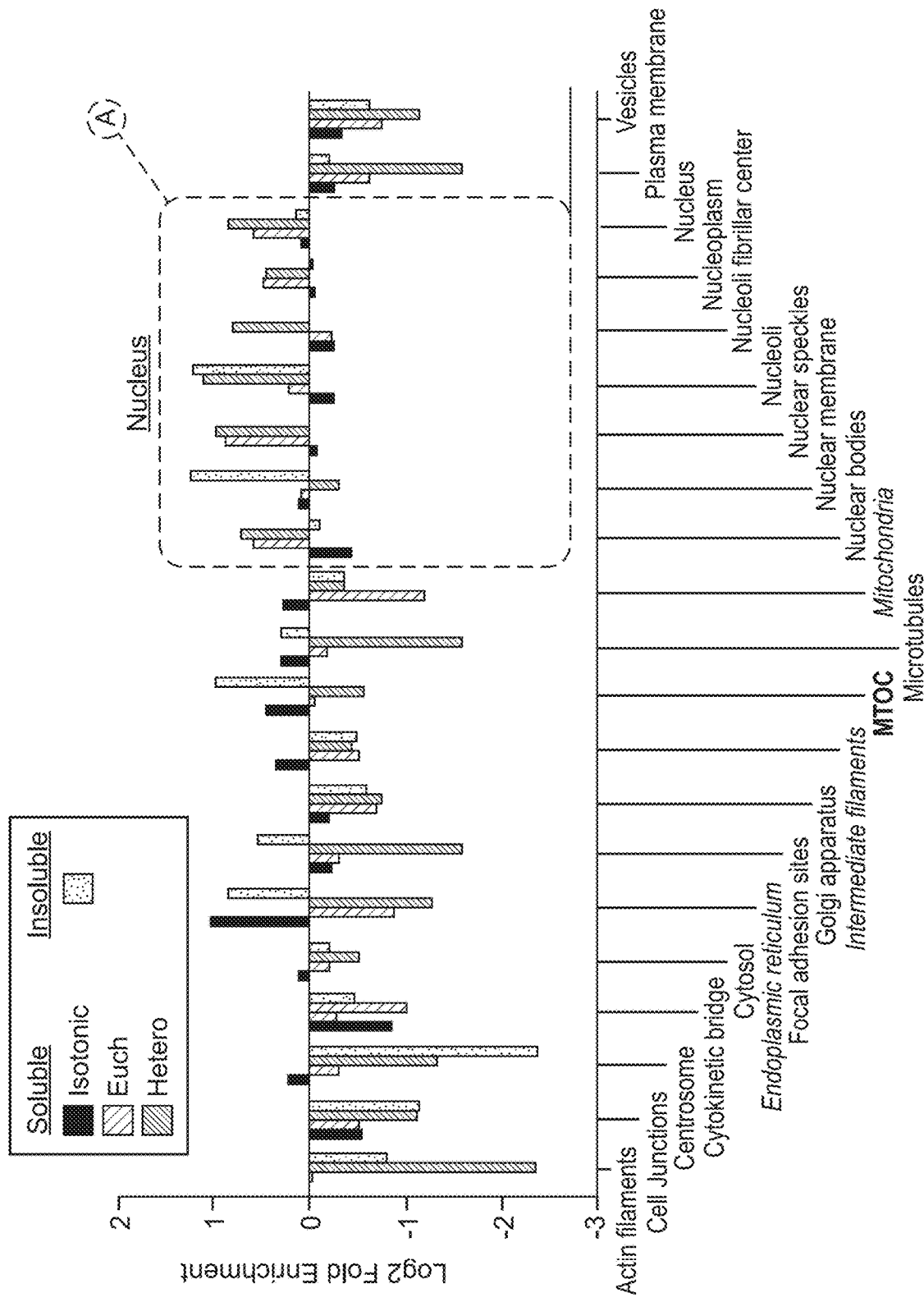
FIG. 12B shows that chromatin fractions are associated with the modes of gross nuclear organization by comparing extraction data with the Human Protein Atlas.
Figure 12B:
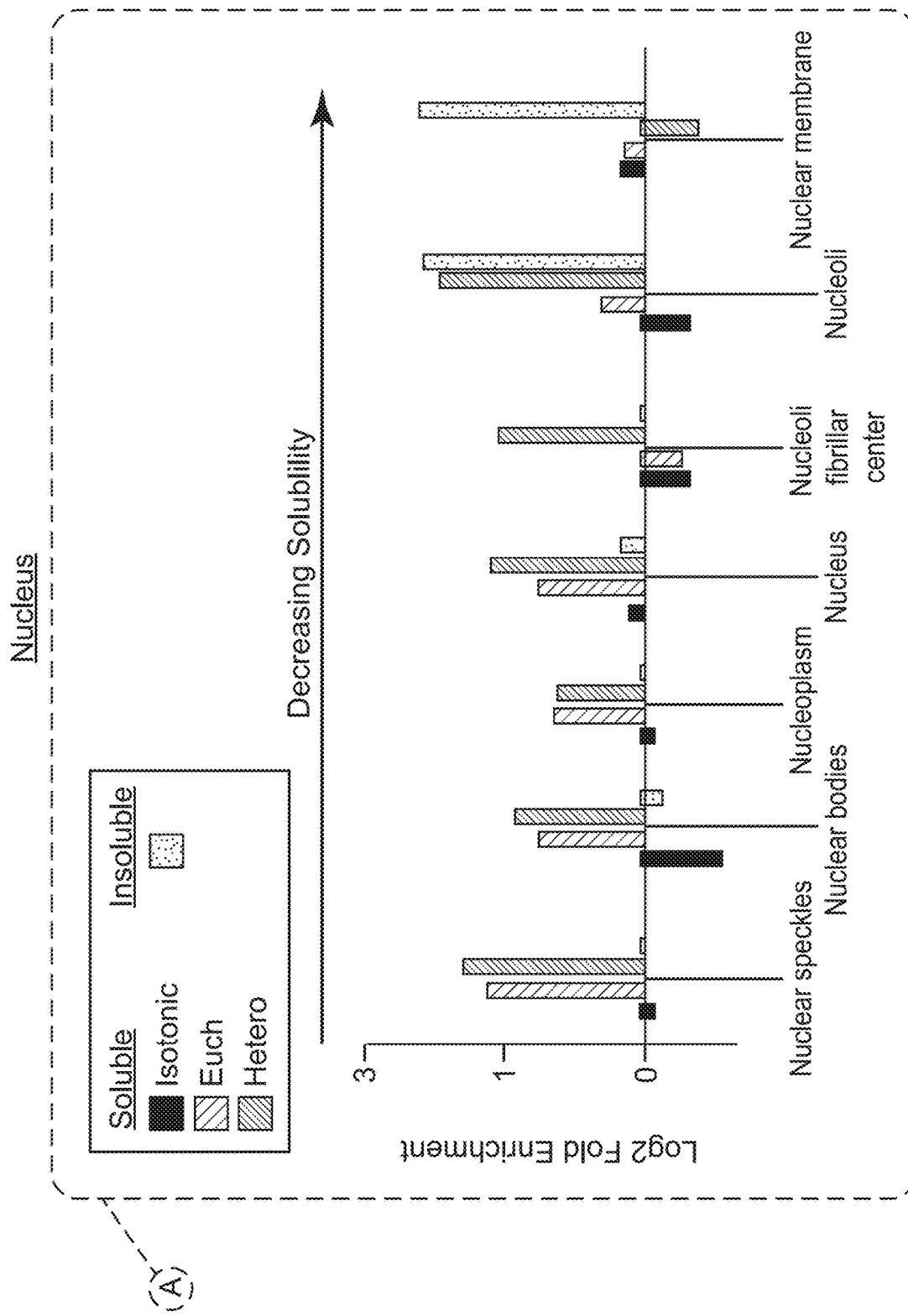

This example shows transcription factors were extracted in the chromatin fraction that was associated with their known function. FIG. 12A shows immunofluorescence of the nucleus (DAPI), acetylated histones (H3K27ac), and euchromatin transcription factor (GATA1) during euchromatin extraction. GATA1 was completely extracted while H3K27ac remained in the nucleus. FIG. 12B shows that chromatin fractions are associated with the modes of gross nuclear organization by comparing extraction data with the Human Protein Atlas.

Example 9

Comparing Nuclear Proteomes Across Differentiating Cells

Figure 13:
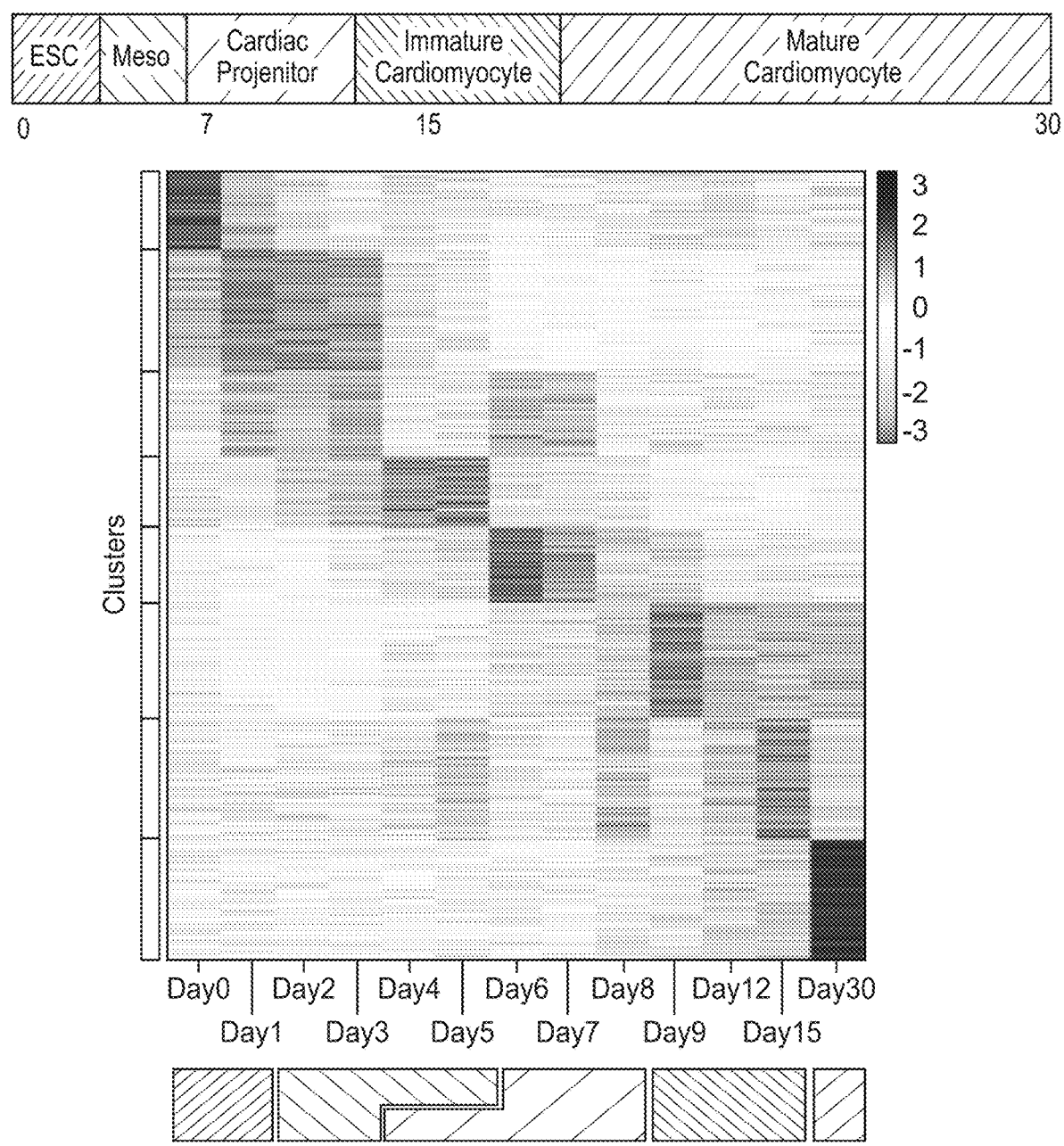
FIG. 13 shows the differentiation of human embryonic stem cells into cardiomyocytes using chromatin proteomic profiling. These data highlight the transcription factor dynamics within the euchromatin fraction, including known and novel potential regulators of cardiac development.
Figure 13:
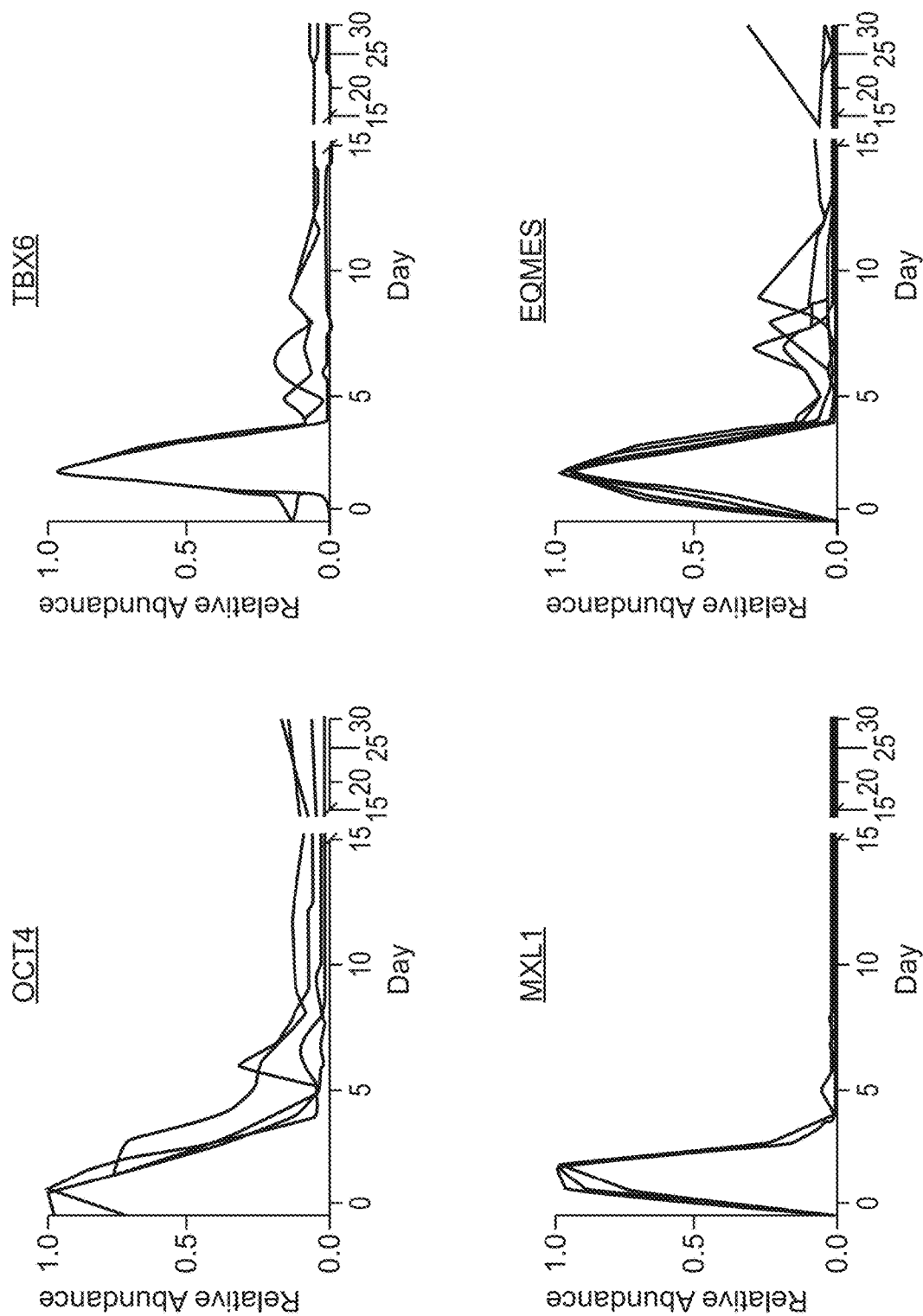
Figure 13:
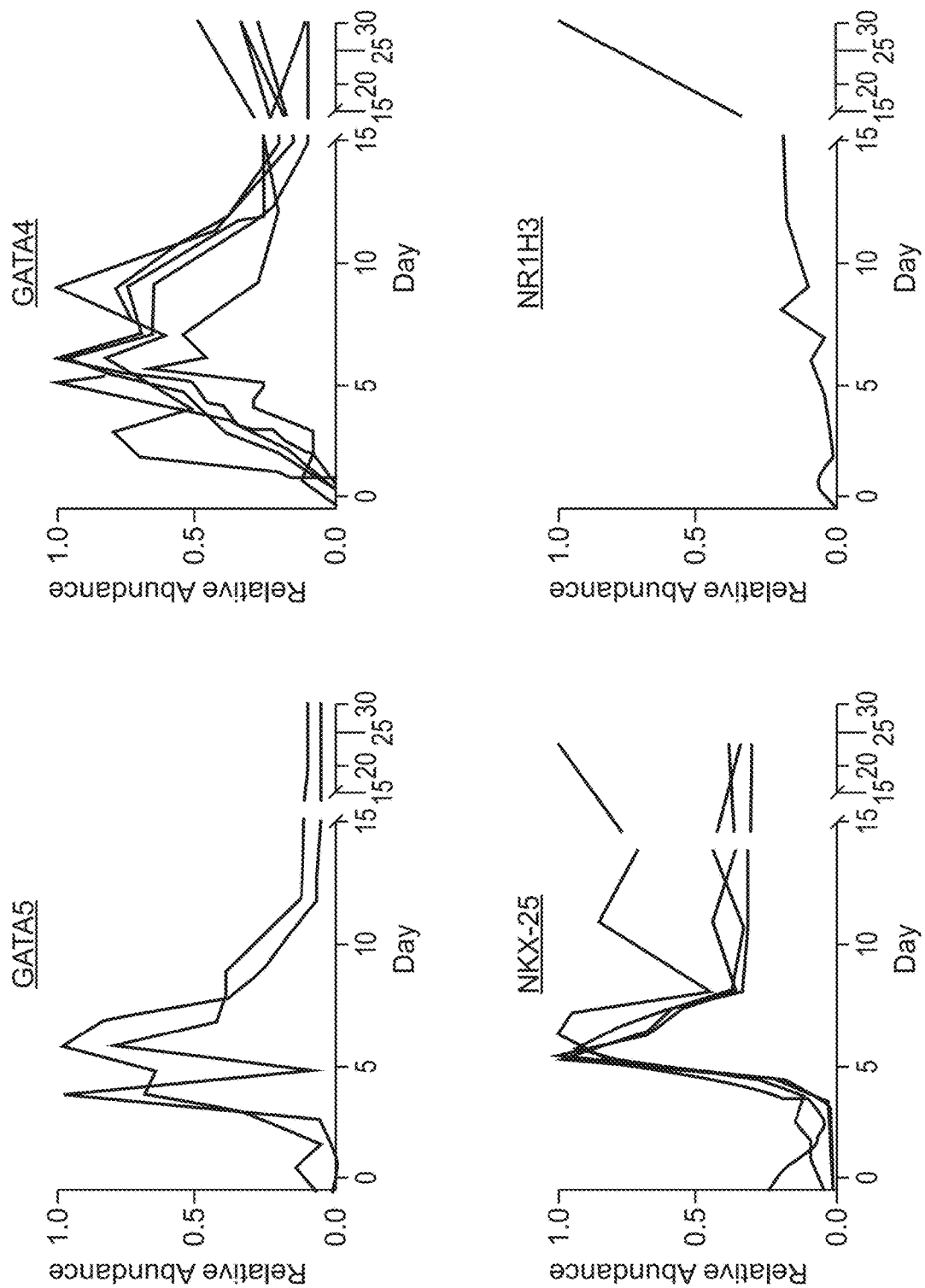

This example shows the methods described herein may used to assess the nuclear proteome at different stages of cell differentiation. FIG. 13 shows the differentiation of human embryonic stem cells into cardiomyocytes using chromatin proteomic profiling as described herein. These data highlight the transcription factor dynamics within the euchromatin fraction, including known and novel potential regulators of cardiac development.

Example 10

Comparing Nuclear Proteomes Across Different Conditions

Figure 14:
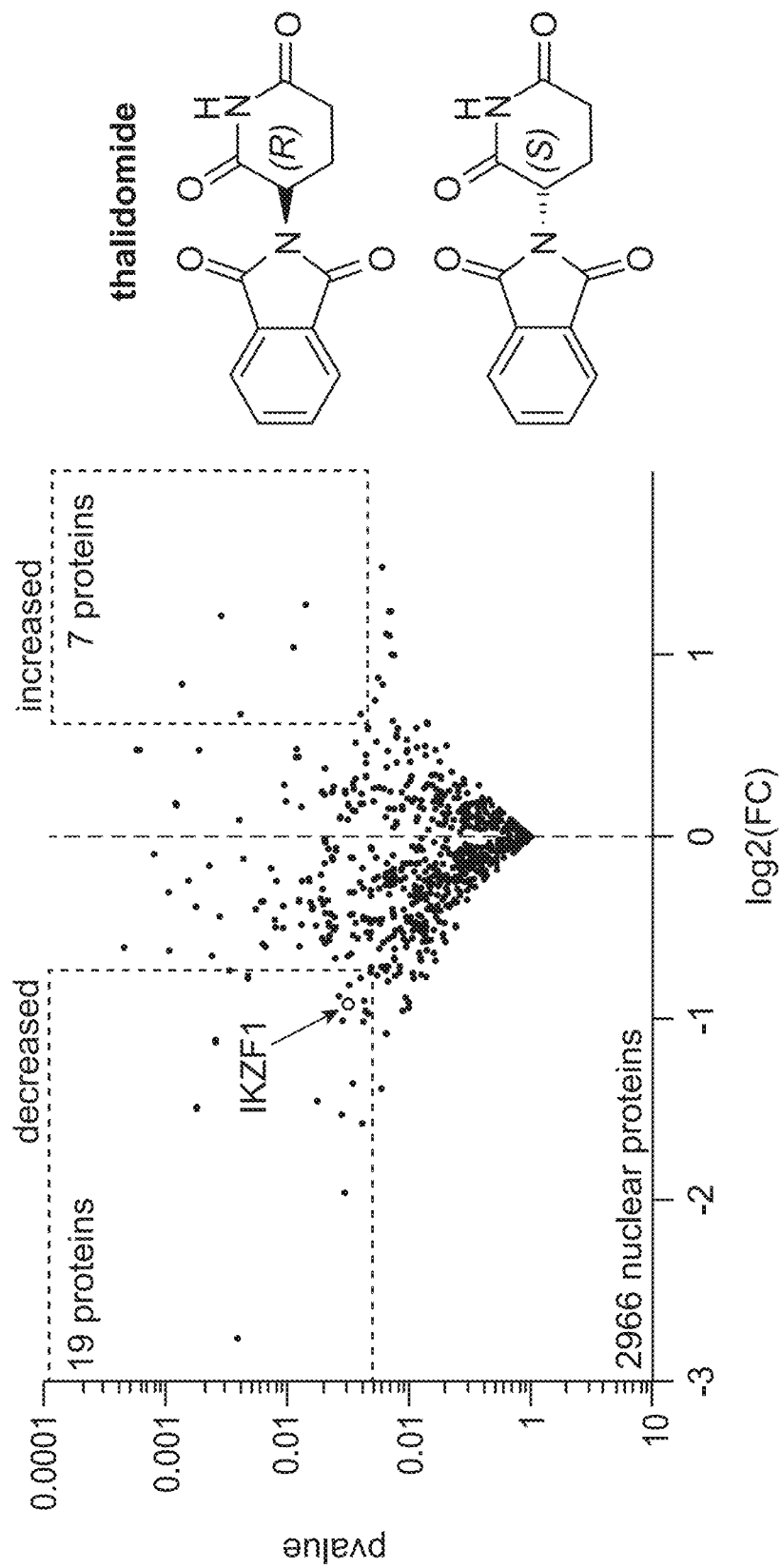
FIG. 14 shows the detection of pharmacological degradation or increased protein expression after cell treatment with thalidomide.

This example shows the methods described herein may be used to compare nuclear proteomes across different conditions (such as physical or chemical environments, including different temperatures, different acidities or alkalinities, different buffering conditions, etc., or any combination thereof). A method for comparing nuclear proteomes across different conditions is comprised of: preparing cells from a first condition by (a) preparing a first suspension solution with buffer A not comprising polycations and a second suspension solution comprising the first suspension solution and a salt; (b) adding a detergent solution to isolate the cell nuclei of the cells; (c) re-suspending the cells in the second suspension solution; (d) quenching the cells; and (e) pelleting insoluble chromatin from the second suspension solution; and preparing cells from a second condition by (a) preparing a first suspension solution with buffer A not comprising polycations and a second suspension solution comprising the first suspension solution and a salt; (b) adding a detergent solution to isolate the cell nuclei of the cells; (c) re-suspending the cells in the second suspension solution; (d) quenching the cells; and (e) pelleting insoluble chromatin from the second suspension solution. The nuclear proteome of the cells from the first condition is determined by mass spectrometry of the cells from the first condition prepared by (a)-(e) and compared with the nuclear proteome of the cells from the second condition, which is determined by mass spectrometry of the cells from the second condition prepared by (a)-(e). The method is further comprised of any additional operations disclosed herein with respect to any of the methods disclosed herein. The method is repeated for one or more iterations (such as at least 1, at least 2, at least 5, at least 10, at least 20, at least 50, at least 100, at least 200, at least 500, or at least 1,000 iterations) under a different set of physical or chemical conditions at each iteration. FIG. 14 shows the detection of pharmacological degradation or increased protein expression after cell treatment with thalidomide. As expected, IKZF1 was shown to be degraded after cell treatment with thalidomide.

Example 11

Characterizing Small Molecule Degradation Compounds

Figure 15:
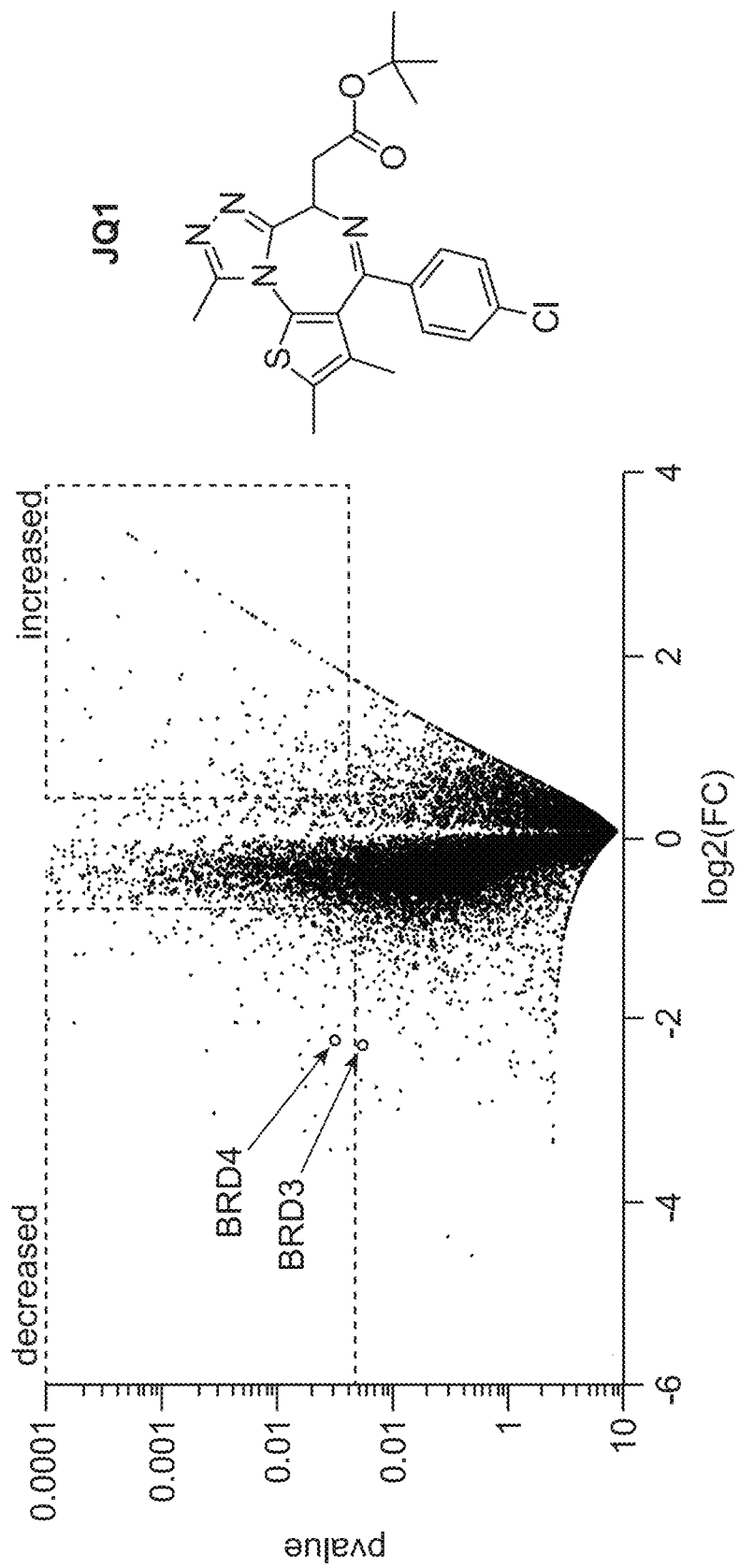
FIG. 15 shows the detection of pharmacological degradation or increased protein expression after cell treatment with JQ1, an inhibitor of the BET family of bromodomain proteins.

This example shows the methods described herein may be used to characterize small molecule degradation compounds. A method for characterizing small molecule degradation compounds is comprised of treating cells with a small molecule degradation compound and then: (a) preparing a first suspension solution with buffer A not comprising polycations and a second suspension solution comprising the first suspension solution and a salt; (b) adding a detergent solution to isolate the cell nuclei of the cells; (c) re-suspending the cells in the second suspension solution; (d) quenching the cells; and (e) pelleting insoluble chromatin from the second suspension solution. The nuclear proteome of the cells treated with small molecule degradation compounds is determined by mass spectrometry of the cells prepared by (a)-(e). The nuclear proteome of the cells treated with small molecule degradation compounds is compared to the nuclear proteome of cells not treated with the small molecule degradation compounds. The method is further comprised of any additional operations disclosed herein with respect to any of the methods disclosed herein. FIG. 15 shows the detection of pharmacological degradation of proteins after cell treatment with JQ1, an inhibitor of the BET family of bromodomain proteins. As expected, BRD4 and BRD3 were shown to be degraded after cell treatment with JQ1.

Example 12

Assaying Cellular Thermal Shifts

Figure 16:
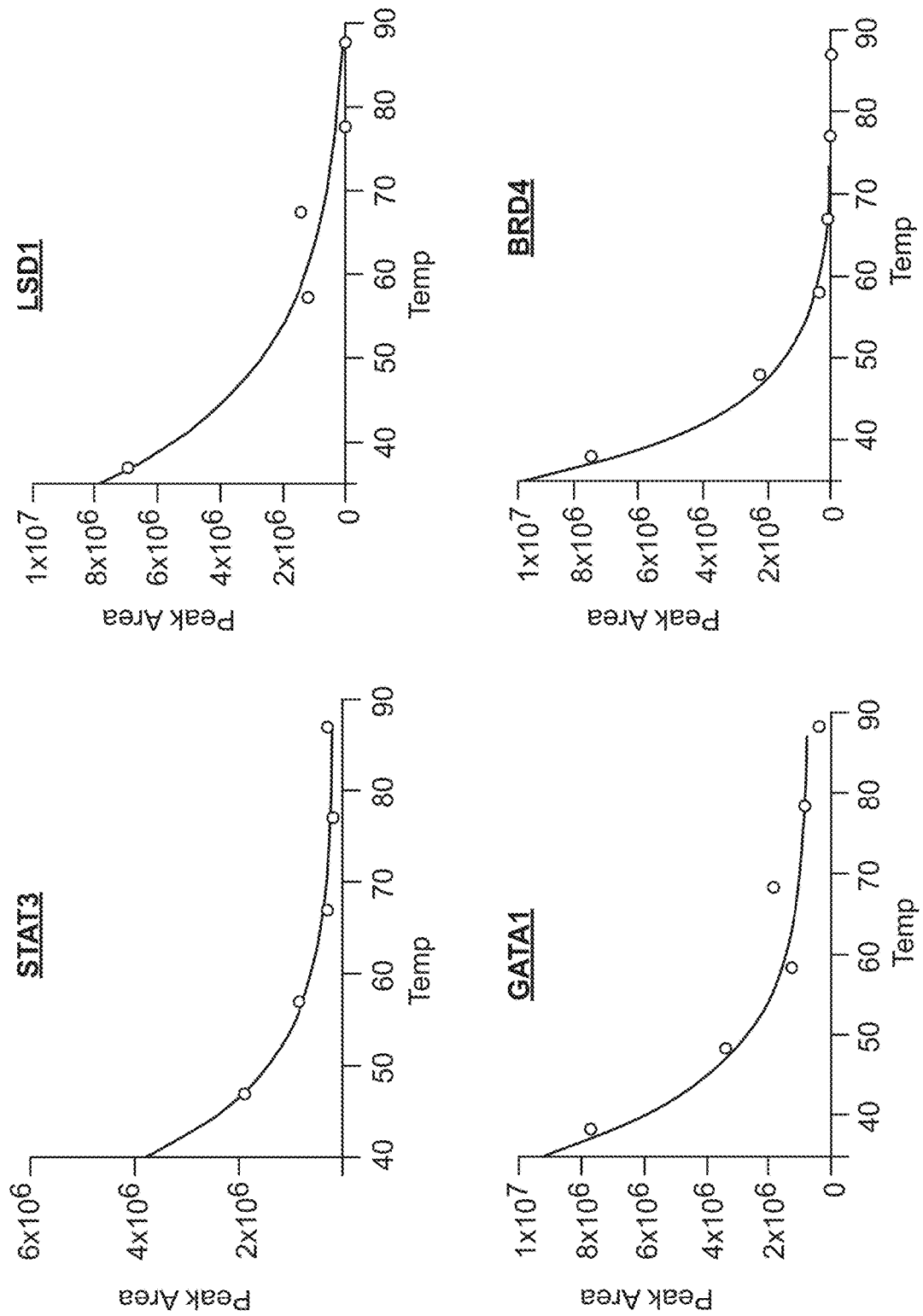
FIG. 16 shows the melting curves of four proteins, STAT5, LSD1, GATA1, and BRD4.

This example shows the methods described herein may be used to assay cellular thermal shifts. A method for assaying cellular thermal shifts is comprised of: (a) preparing a first suspension solution with buffer A not comprising polycations and a second suspension solution comprising the first suspension solution and a salt; (b) adding a detergent solution to isolate the cell nuclei of the cells; (c) re-suspending the cells in the second suspension solution; (d) quenching the cells; and (e) pelleting insoluble chromatin from the second suspension solution. The method is further comprised of any additional operations disclosed herein with respect to any of the methods disclosed herein. The method is repeated for one or more iterations (such as at least 1, at least 2, at least 5, at least 10, at least 20, at least 50, at least 100, at least 200, at least 500, or at least 1,000 iterations) under a different set of thermal conditions for each iteration. FIG. 16 shows the melting curves of four proteins, STAT3, LSD1, GATA1, and BRD4.

Example 13

Characterizing Genome Edits

Figure 17:
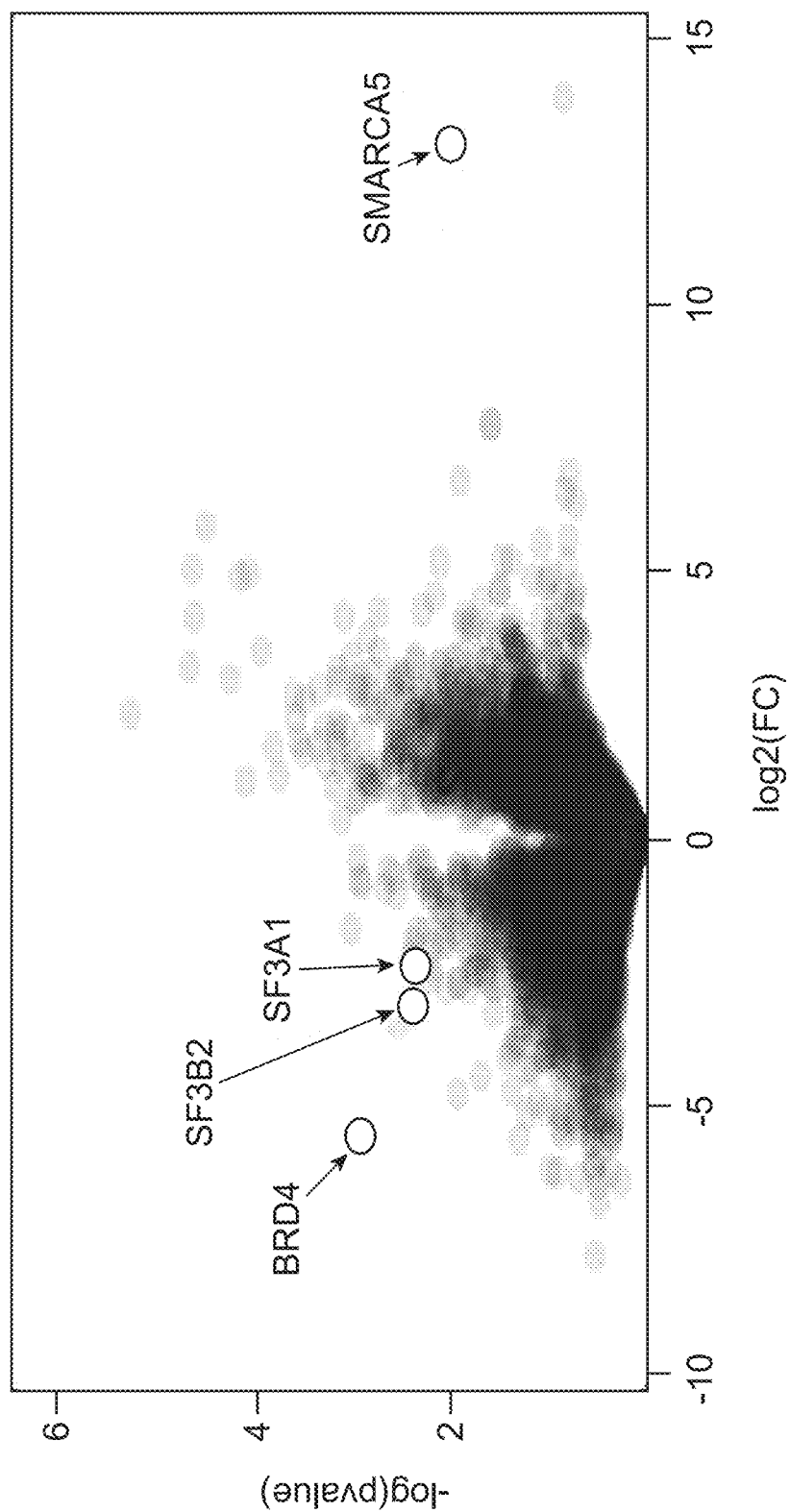
FIG. 17 shows differential protein abundance in wild-type cell lines versus an engineered BRD4 dominant negative point mutation cell line.

This example shows the methods described herein may be used to characterize genome edits. A method for characterizing genome edits is comprised of: providing edited cells and then: (a) preparing a first suspension solution with buffer A not comprising polycations and a second suspension solution comprising the first suspension solution and a salt; (b) adding a detergent solution to isolate the cell nuclei of the cells; (c) re-suspending the cells in the second suspension solution; (d) quenching the cells; and (e) pelleting insoluble chromatin from the second suspension solution. The method is further comprised of any additional operations disclosed herein with respect to any of the methods disclosed herein. The method is applied to characterize genome edits induced using any genome editing technology, including but not limited to CRISPR-based genome editing techniques, transcription activator-like effector nuclease (TALEN)-based genome editing techniques, or zinc finger nuclease (ZFN)-based genome editing techniques. FIG. 17 shows differential protein abundance in wild-type cell lines versus an engineered BRD4 dominant negative point mutation cell line.

Example 14

Characterizing Small Molecule Degradation Compounds

This example shows that systems-wide pharmacological response of the nuclear proteome is detected after treatment with chromatin-active drugs using the methods described herein. New classes of proteolysis targeting chimer (PROTAC) compounds that degrade their protein targets or their non-degrading chemical isoforms were administered to cells. The nuclear proteome was detected using the methods as previously described for cells both before and after treatment with PROTACs or their non-degrading chemical isoforms. The detected nuclear proteomes showed that PROTACs have differential effects on the transcriptional network in comparison to their non-degrading chemical isoforms.

What is claimed is:

1. A method for isolating samples enriched in nucleoplasm associated transcription factors, euchromatin associated transcription factors, and heterochromatin associated transcription factors from cells, the method comprising:
   (a) suspending cells in a first buffer that does not comprise polycations;
   (b) adding a detergent solution to the suspended cells;
   (c) separating nuclei from the cells following (b); and
   sequentially extracting the nucleoplasm associated transcription factors, euchromatin associated transcription factors, and heterochromatin associated transcription factors from the separated nuclei as follows:
   (d) re-suspending the nuclei of (c) in a second buffer not comprising polycations but comprising ethylenediaminetetraacetic acid (EDTA) and salt;
   (e) separating insoluble chromatin after (d);
   (f) collecting a first supernatant liquid after (e), wherein the first supernatant liquid is enriched for nucleoplasm associated transcription factors;
   (g) re-suspending the insoluble chromatin of (e) in a third buffer not comprising polycations but comprising EDTA and an increased salt concentration as compared to the second buffer to extract euchromatin associated transcription factors;
   (h) separating insoluble chromatin after (g);
   (i) collecting a second supernatant liquid after (g), wherein the second supernatant liquid is enriched for euchromatin associated transcription factors;
   (j) re-suspending the insoluble chromatin of (h) in a fourth buffer not comprising polycations but comprising EDTA and an increased salt concentration as compared to the third buffer to extract heterochromatin associated transcription factors;
   (k) separating insoluble chromatin after (j); and
   (l) collecting a third supernatant liquid after (k), wherein the third supernatant liquid is enriched for heterochromatin associated transcription factors,
   wherein the method further comprises analyzing and identifying the nucleoplasm associated transcription factors in the first supernatant liquid, the euchromatin associated transcription factors in the second supernatant liquid, and/or the heterochromatin associated transcription factors in the third supernatant liquid by mass spectrometry, and
   wherein histone proteins remain in the insoluble chromatin of (k).

2. The method of claim 1, wherein (e) comprises separating insoluble chromatin by pelleting, the method further comprising:
   (m) re-suspending the pelleted insoluble chromatin of (e) in a fifth buffer not comprising polycations but comprising salt;
   (n) separating insoluble chromatin after (m); and
   (o) collecting a fourth supernatant liquid after (n), wherein the fourth supernatant liquid comprises nuclear proteins.

3. The method of claim 1, wherein the method compares nucleoplasm associated transcription factors, euchromatin associated transcription factors, and heterochromatin associated transcription factors across different cell conditions, the method comprising:
   preparing first, second, and third supernatant liquids from cells from a first condition by steps (a)-(l);
   preparing first, second, and third supernatant liquids from cells from a second condition by steps (a)-(l); and
   comparing the nucleoplasm associated transcription factors, the euchromatin associated transcription factors, and the heterochromatin associated transcription factors determined by mass spectrometry of the first, second, and third supernatant liquids from the cells from the first condition to the nucleoplasm associated transcription factors, the euchromatin associated transcription factors, and the heterochromatin associated transcription factors determined by mass spectrometry of the first, second and third supernatant liquids from cells from the second condition.

4. The method of claim 1, wherein the method characterizes small molecule degradation compounds, the method comprising:
   preparing first, second, and third supernatant liquids from cells treated with a small degradation compound by steps (a)-(l); and
   characterizing the nucleoplasm associated transcription factors, the euchromatin associated transcription factors, and the heterochromatin associated transcription factors determined by mass spectrometry of the first, second, and third supernatant liquids.

5. The method of claim 1, wherein the method assays thermal stability of nucleoplasm associated transcription factors, euchromatin associated transcription factors, and heterochromatin associated transcription factors, the method comprising:
   preparing first, second, and third supernatant liquids from a first thermal condition by steps (a)-(l);
   preparing first, second, and third supernatant liquids from a different thermal condition by steps (a)-(l); and
   comparing the nucleoplasm associated transcription factors, the euchromatin associated transcription factors, and the heterochromatin associated transcription factors determined by mass spectrometry of the first, second, and third supernatant liquids from the first thermal condition to a nuclear proteome determined by mass spectrometry of the first, second, and third supernatant liquids from the different thermal condition.

6. The method of claim 1, wherein the method characterizes genome edits, the method comprising:
preparing first, second, and third supernatant liquids from genome edited cells by steps (a)-(l); and
comparing the nucleoplasm associated transcription factors, the euchromatin associated transcription factors, and the heterochromatin associated transcription factors determined by mass spectrometry of the first, second, and third supernatant liquids prepared from the genome edited cells to the nuclear proteome determined by mass spectrometry of first, second, and third supernatant liquids prepared by steps (a)-(l) from wild type cells.

7. The method of claim 1, further comprising harvesting, homogenizing, washing, or pelleting the cells before (a).

8. The method of claim 1, further comprising incubating the nuclei between (d) and (e).

9. The method of claim 8, wherein the nuclei are incubated at a temperature of about 4° C.

10. The method of claim 8, wherein the nuclei are incubated for a period of about 30 minutes.

11. The method of claim 1, wherein the detergent solution comprises NP40 at a concentration of from about 0.1% to about 4%.

12. The method of claim 1, wherein the salt comprises sodium chloride (NaCl).

13. The method of claim 1, wherein the nucleoplasm associated transcription factors, euchromatin associated transcription factors, and heterochromatin associated transcription factors comprise one or more of OCT4, TBX6, MXL1, EQMES, GATA5, GATA4, NKX-25, NR1H3, STAT3, LSD1, GATA1, BRD4, BRD4, SF3B2, SF3A1, and SMARCA5.

14. The method of claim 1, further comprising adding a surfactant to the first, second, or third supernatant liquid and/or separated insoluble chromatin following step (e), (h), and/or (k).

15. A method for isolating samples enriched in nuclear transcription factors from cells, the method comprising:
(a). suspending cells in a buffer that does not comprise polycations;
(b). adding a detergent solution to the suspended cells, optionally wherein the detergent comprises NP40;
(c). separating nuclei from the cells following (b);
(d). contacting the separated nuclei of (c) with ethylenediaminetetraacetic acid (EDTA); and
(e). sequentially extracting nucleoplasm associated transcription factors, euchromatin associated transcription factors, and heterochromatin associated transcription factors from the separated nuclei following (d) by sequentially re-suspending the nuclei in buffers not comprising polycations but comprising increasing salt concentrations, separating insoluble chromatin following each sequential re-suspension, and collecting a supernatant liquid after the insoluble chromatin is separated following each sequential re-suspension,
wherein the method further comprises analyzing and identifying the nucleoplasm associated transcription factors, the euchromatin associated transcription factors, and the heterochromatin associated transcription factors in the supernatant liquids by mass spectrometry, and
wherein histone proteins remain in the insoluble chromatin after (e).

* * * * *